United States Patent
Starkebaum et al.

[11] Patent Number: 6,122,548
[45] Date of Patent: Sep. 19, 2000

[54] SYSTEM AND METHOD FOR PREVENTING CROSS-CONDUCTION IN A HUMAN-IMPLANTABLE DUAL CHANNEL NEUROSTIMULATOR

[75] Inventors: Warren Starkebaum, Plymouth; Mark T. Rise, Monticello, both of Minn.; Donald L. Hall, Mesa; Marc T. Stein, Chandler, both of Ariz.

[73] Assignee: Medtronic, Inc., Minneapolis, Minn.

[21] Appl. No.: 09/348,896

[22] Filed: Jul. 7, 1999

Related U.S. Application Data

[63] Continuation of application No. 08/847,651, Apr. 30, 1997, Pat. No. 5,948,007.

[51] Int. Cl.[7] .................................. A61N 1/05; A61N 1/34
[52] U.S. Cl. .................................................. 607/67; 607/46
[58] Field of Search ................................. 607/66, 67, 46, 607/5, 55–57

[56] References Cited

U.S. PATENT DOCUMENTS

| | | |
|---|---|---|
| 3,774,620 | 11/1973 | Hansjurgens . |
| 3,895,639 | 7/1975 | Rodler . |
| 4,071,033 | 1/1978 | Nawracaj et al. . |
| 4,338,945 | 7/1982 | Kosugi et al. . |
| 4,640,286 | 2/1987 | Thomson . |
| 4,803,988 | 2/1989 | Thomson . |
| 4,813,418 | 3/1989 | Harris . |
| 4,856,525 | 8/1989 | Van den Honert . |
| 5,117,826 | 6/1992 | Bartelt et al. . |
| 5,269,304 | 12/1993 | Matthews . |
| 5,522,853 | 6/1996 | Kroll ........................................... 607/5 |
| 5,643,330 | 7/1997 | Holsheimer et al. . |
| 5,674,266 | 10/1997 | Stendahl . |
| 5,690,686 | 11/1997 | Min et al. . |
| 5,713,922 | 2/1998 | King . |
| 5,766,226 | 6/1998 | Pedersen ..................................... 607/5 |
| 5,913,877 | 6/1999 | Kroll et al. . |
| 5,925,070 | 7/1999 | King et al. ............................... 607/46 |

*Primary Examiner*—Carl H. Layno
*Attorney, Agent, or Firm*—Banner & Witcoff, Ltd.

[57] ABSTRACT

Undesirable cross-conduction between electrode pairs in a human-implantable dual channel neurostimulator is prevented. The first and second pairs of electrodes may, optionally, share a common electrode. The first electrode pair is stimulated and then recharged. Then, after a finite waiting period has elapsed, the second electrode pair is stimulated and then recharged. Then, after a finite waiting period, the process is repeated. A high impedance state is established across one of the electrode pairs while the other electrode pair is being stimulated and recharged. Such a high impedance state prevents current from flowing through one of the electrode pairs while the other electrode pair is being stimulated or recharged.

7 Claims, 43 Drawing Sheets

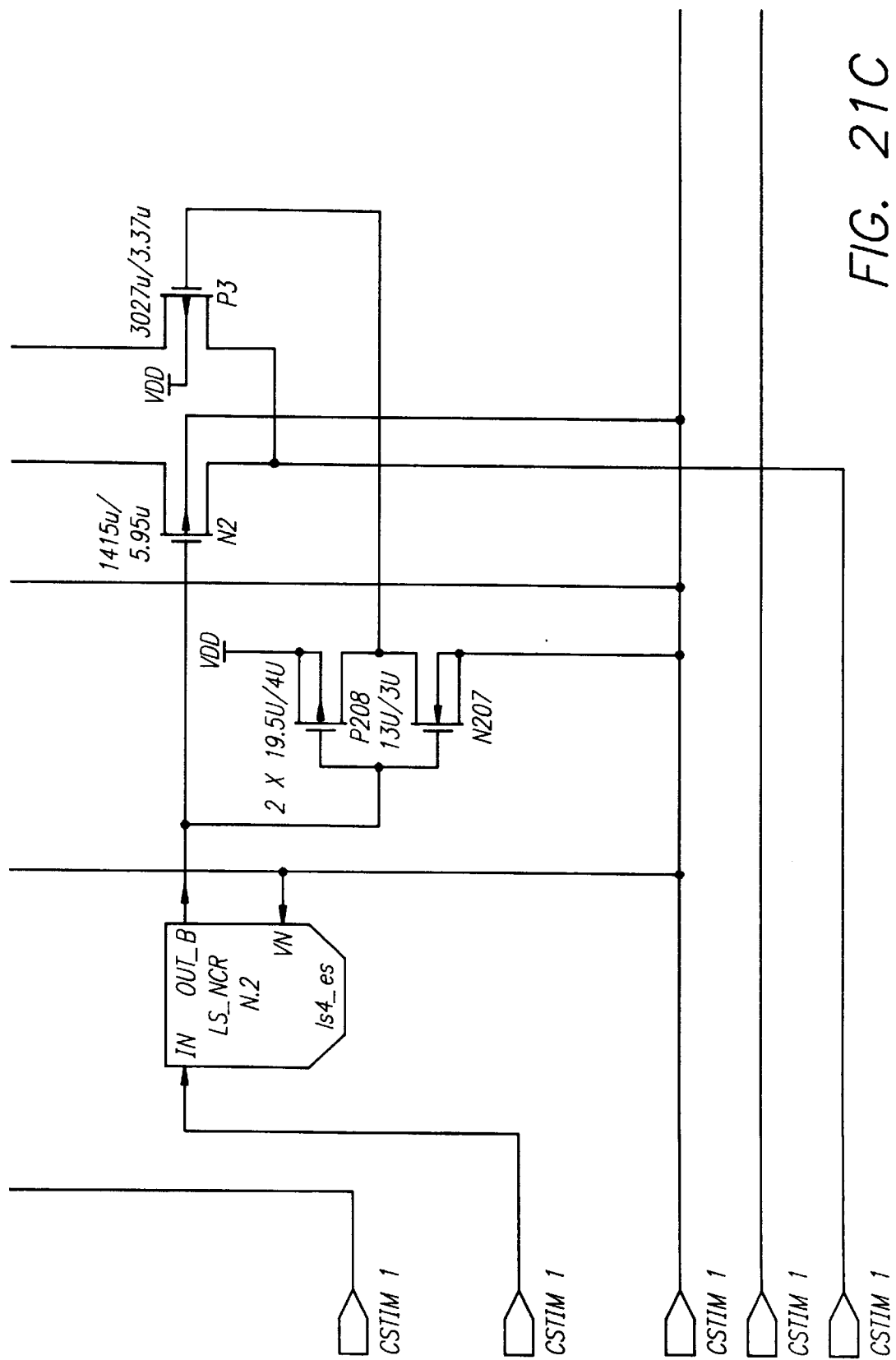

SYSTEM AND METHOD FOR PREVENTING CROSS-CONDUCTION IN A HUMAN-IMPLANTABLE DUAL CHANNEL NEUROSTIMULATOR

RELATED APPLICATIONS

This application is a continuation of Starkebaum et al. U.S. Ser. No. 08/847,651, filed Apr. 30, 1997, assigned to Medtronic, Inc., which issued as U.S. Pat. No. 5,948,007 on Sep. 7, 1999.

BACKGROUND OF THE INVENTION

1. Field of the Invention

This invention relates to means of stimulating electrically excitable tissue, and more particularly relates to means for adjusting the locus at which action potentials are induced in such tissue.

2. Description of the Related Art

Two major practical problems reduce the efficacy of epidural spinal cord stimulation (SCS) for pain control. One is the difficulty of directing the stimulation-induced paresthesia to the desired body part and the other is the problem of disagreeable sensations or motor responses to the stimulation, which reduce the comfortable amplitude range of the stimulation. It is generally agreed that in SCS, for chronic pain, paresthesia should cover the whole pain region. With present stimulation methods and equipment, only highly skilled and experienced practitioners are able to position a stimulation lead in such a way that the desired overlap is reached and desired results are obtained over time with minimal side effects. It requires much time and effort to focus the stimulation on the desired body region during surgery and, with single channel approaches, it is difficult to redirect it afterwards, even though some readjustments can be made by selecting a different contact combination, pulse rate, pulse width or voltage.

Redirecting paresthesia after surgery is highly desirable. Even if paresthesia covers the pain area perfectly during surgery, the required paresthesia pattern often changes later due to lead migration, or histological changes (such as the growth of connective tissue around the stimulation electrode) or disease progression. The problem of lead placement has been addressed by U.S. Pat. No. 5,121,754 by the use of a lead with a deformable distal shape. These problems are not only found with SCS, but also with peripheral nerve stimulation (PNS), depth brain stimulation (DBS), cortical stimulation and also muscle or cardiac stimulation.

A system capable of some adjustment of spinal cord excitation is described in PCT International Publication No. WO 95/19804. However, that system requires three electrodes, optimally spaced, which is a serious handicap during the surgical procedure required in order to place these electrodes in the body. Three electrodes may require the use of a paddle arrangement which is surgically difficult to manipulate adjacent the spinal cord. In addition, that system has only limited adjustment capability, dependent on the distance from the electrodes to the spinal cord.

SUMMARY OF THE INVENTION

This invention may be advantageously used to prevent undesirable cross-conduction between electrode pairs in a human-implantable dual channel neurostimulator in which the first and second pairs of electrodes may, optionally, share a common electrode. According to a preferred embodiment of the invention, the first electrode pair is stimulated and then recharged. Then, after a finite waiting period has elapsed, the second electrode pair is stimulated and then recharged. Then, after a finite waiting period, the process is repeated such that the first electrode pair is stimulated and then recharged followed by a waiting period, and then the second electrode pair is stimulated and then recharged followed by a waiting period.

The first pair of electrodes is coupled to a first circuit, which includes a first plurality of switches. The first plurality of switches includes a first subset of switches and a second subset of switches. Each of the first plurality of switches is opened during the waiting periods and while stimulating and recharging the second pair of electrodes. The first subset of switches of the first plurality of switches is closed while stimulating the first pair of electrodes, and the second subset of switches of the first plurality of switches is closed while recharging the first pair of electrodes.

Similarly, the second pair of electrodes is coupled to a second circuit, which includes a second plurality of switches. The second plurality of switches includes a first subset of switches and a second subset of switches. Each of the second plurality of switches is opened during the waiting periods and while stimulating and recharging the first pair of electrodes. The first subset of switches of the second plurality of switches is closed while stimulating the second pair of electrodes, and the second subset of switches of the second plurality of switches is closed while recharging the second pair of electrodes.

According to another embodiment, first and second circuits may be used for creating a high impedance state across one of the electrode pairs while the other electrode pair is being stimulated and recharged. Such a high impedance state substantially prevents current from flowing through the pair of electrodes that is not being stimulated and then recharged.

BRIEF DESCRIPTION OF THE DRAWINGS

These and other advantages and features of the invention will become apparent upon reading the following detailed description and referring to the accompanying drawings in which like numbers refer to like parts throughout and in which:

FIGS. 21A–21D are schematics of the electrode switches used in each stimulating, recharging, and stimulating or recharging switch depicted in FIG. 9 for the embodiment of FIGS. 15 and 15A–15I.

DESCRIPTION OF THE PREFERRED EMBODIMENTS

Figure 8:
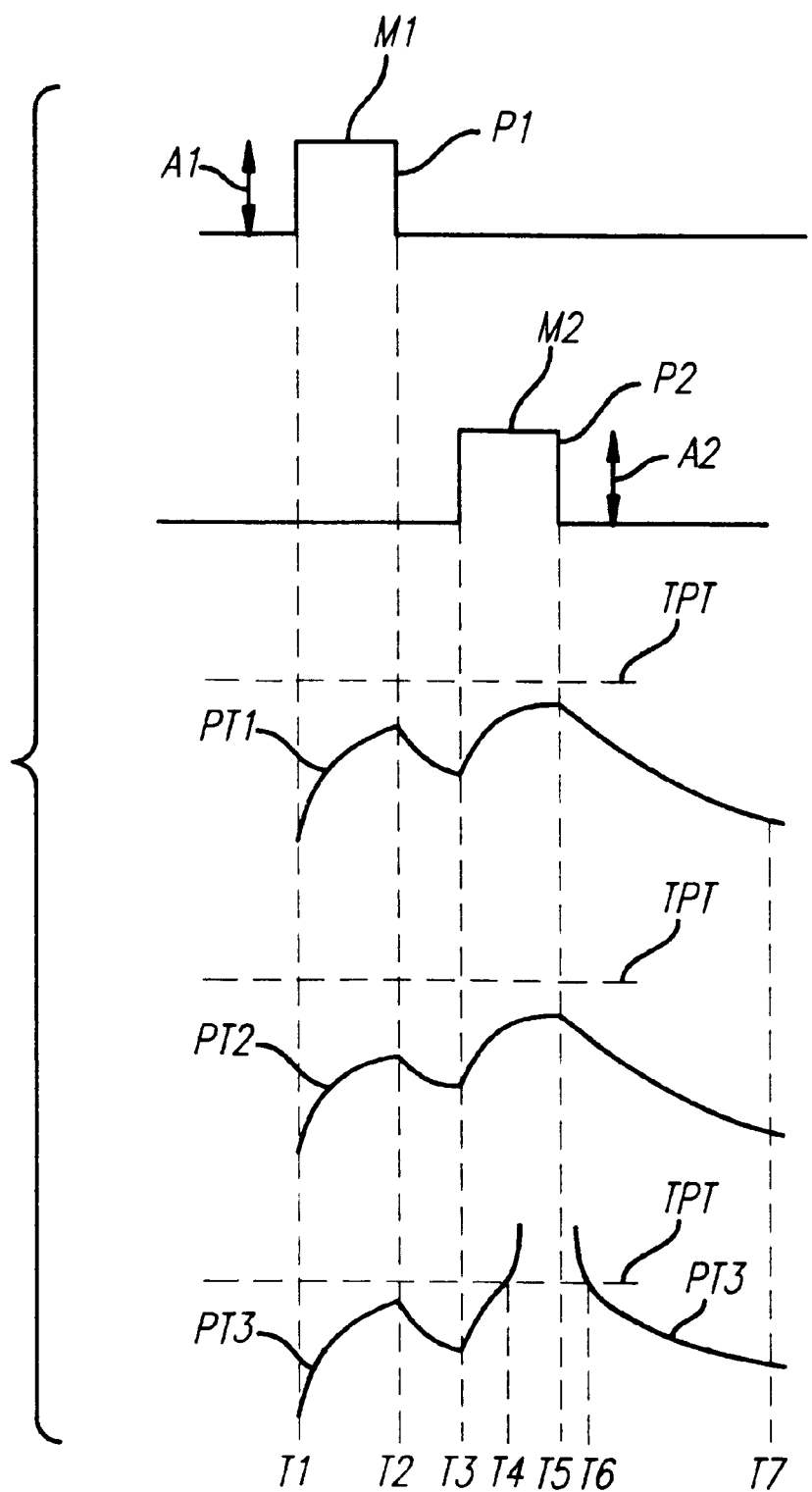
FIG. 8 is a timing diagram showing signals applied to the first and second electrodes illustrated in FIG. 2 in relationship to the potentials induced in tissue adjacent the electrodes.

Referring to FIG. 8, a single electrical signal or pulse, such as P1, can cause depolarization near a cathode in electrically excitable tissue which includes neural tissue and muscle tissue. Neural tissue includes peripheral nerves, the spinal cord surface, deep spinal cord tissue, deep brain tissue, and brain surface tissue. Muscle tissue includes skeletal (red) muscle, smooth (white) muscle, and cardiac muscle. A locus includes a set of points in three-dimensional space and refers to a volume of cells or parts of cells. Due to the electrical characteristics of both the three-dimensional volume conductor and the membrane properties, the potentials outside and inside a neuron respond to the depolarization, usually with exponential-type increases and then attenuation over time. The time constant for an isolated neuron membrane typically is 5–15 milliseconds (*Nerve, Muscle and Synapse* by Bernard Katz, circa 1972). For myelinated axons or muscle cells, it may be considerably shorter.

As shown in FIG. 8, the local depolarization from a single pulse P1 results in a transmembrane potential PT1 between times T1 and T3. The peak of potential PT1 is below the transmembrane potential threshold TPT. As a result, the pulse fails to produce an action potential in that cell.

Action potential is an all-or-none, nonlinear phenomenon, caused by opening of sodium gates, inrush of sodium of ions, and a delayed opening of potassium gates and a restoration of the membrane potential. In general, a certain amount of charge must be passed at the electrodes (amplitude [Volts]/resistance [Ohms]×pulse width [time]) in order to cause enough depolarization for an action potential to begin. There is a reciprocal relationship between amplitude and pulse width: the product must reach a certain value before the threshold is reached. This relationship does not reach the Volts=0 axis. There is a certain minimum voltage needed, called rheobase, before an action potential can happen.

Basic neurophysiological principles, called "electrotonus", show that in any volume of electrically excitable tissue in which two or more pulses, each of which alone is insufficient to bring the cells to threshold, arrive closely together in time, at least part of their effect is additive, i.e., the memory of the first pulse is still present when the second pulse arrives. If the sum of the potentials (distorted by resistive and capacitive properties of the surroundings and the cell membranes) can get some cells depolarized to threshold, then an action potential will start in those cells.

Still referring to FIG. 8, the inducement of an action potential in a cell is illustrated by a transmembrane depolarizing potential PT3 reaching the transmembrane potential threshold TPT at time T4.

Figure 1:
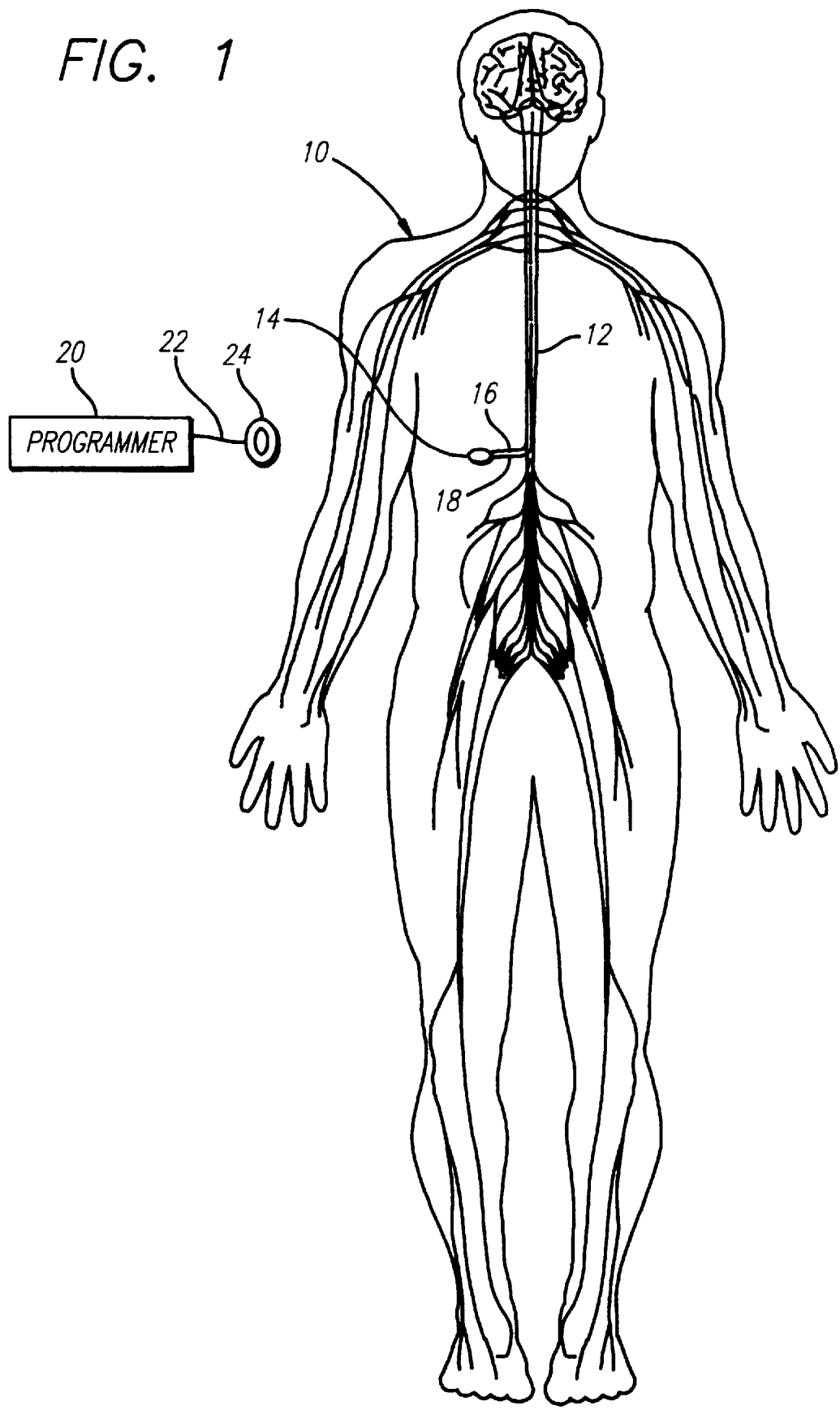
FIG. 1 is a diagrammatic view of a patient in which a preferred form of apparatus for spinal cord stimulation (SCS) made in accordance with the invention has been implanted.
Figure 2:
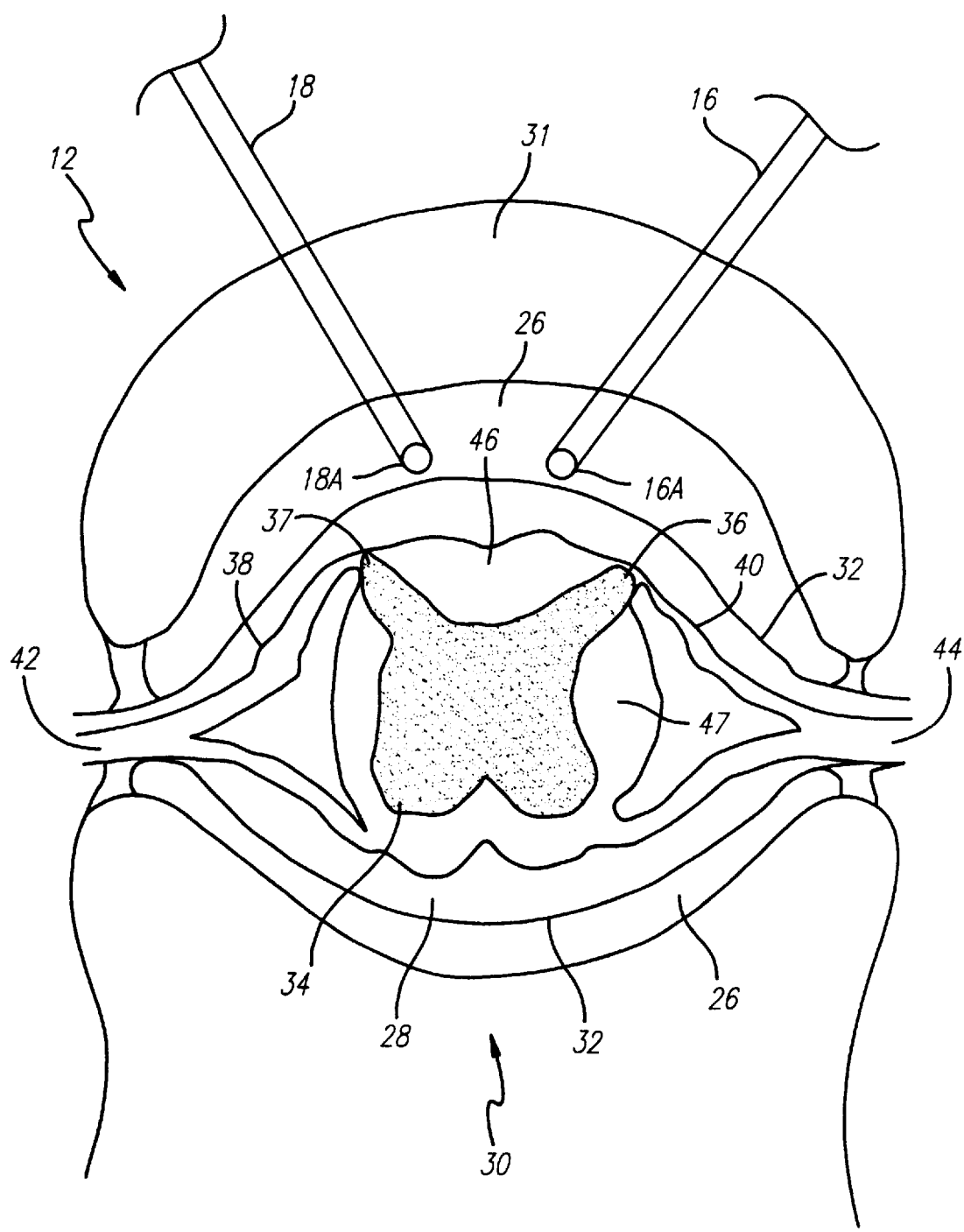
FIG. 2 is a cross-sectional view of an exemplary spinal column showing a typical position at which electrodes made in accordance with the preferred practice of the invention have been implanted in the epidural space.

FIG. 1 is a schematic view of a patient 10 having an implant of a neurological stimulation system employing a preferred form of the present invention to stimulate spinal cord 12 of the patient. The preferred system employs an implantable pulse generator 14 to produce a number of independent stimulation pulses which are sent to spinal cord 12 by insulated leads 16 and 18 coupled to the spinal cord by electrodes 16A and 18A (FIG. 2). Electrodes 16A and 18A also can be attached to separate conductors included within a single lead.

In the preferred embodiment, implantable pulse generator 14 is either a modified ITREL II or a dual channel ITREL ("DCI"). Both models of these implantable pulse generators are commercially available from Medtronic, Inc. and are capable of delivering multiple signals to the one or more electrodes on different channels. The implantable pulse generator 14 can provide multiple signals at different adjustable frequencies, pulse widths, amplitudes, and repetition rates. However, in the DCI implantable pulse generator 14, the repetition rates on the different channels are synchronized. The detailed configuration of the output circuitry utilized in the DCI implantable pulse generator 14 is shown in FIGS. 9–14.

Figure 9:
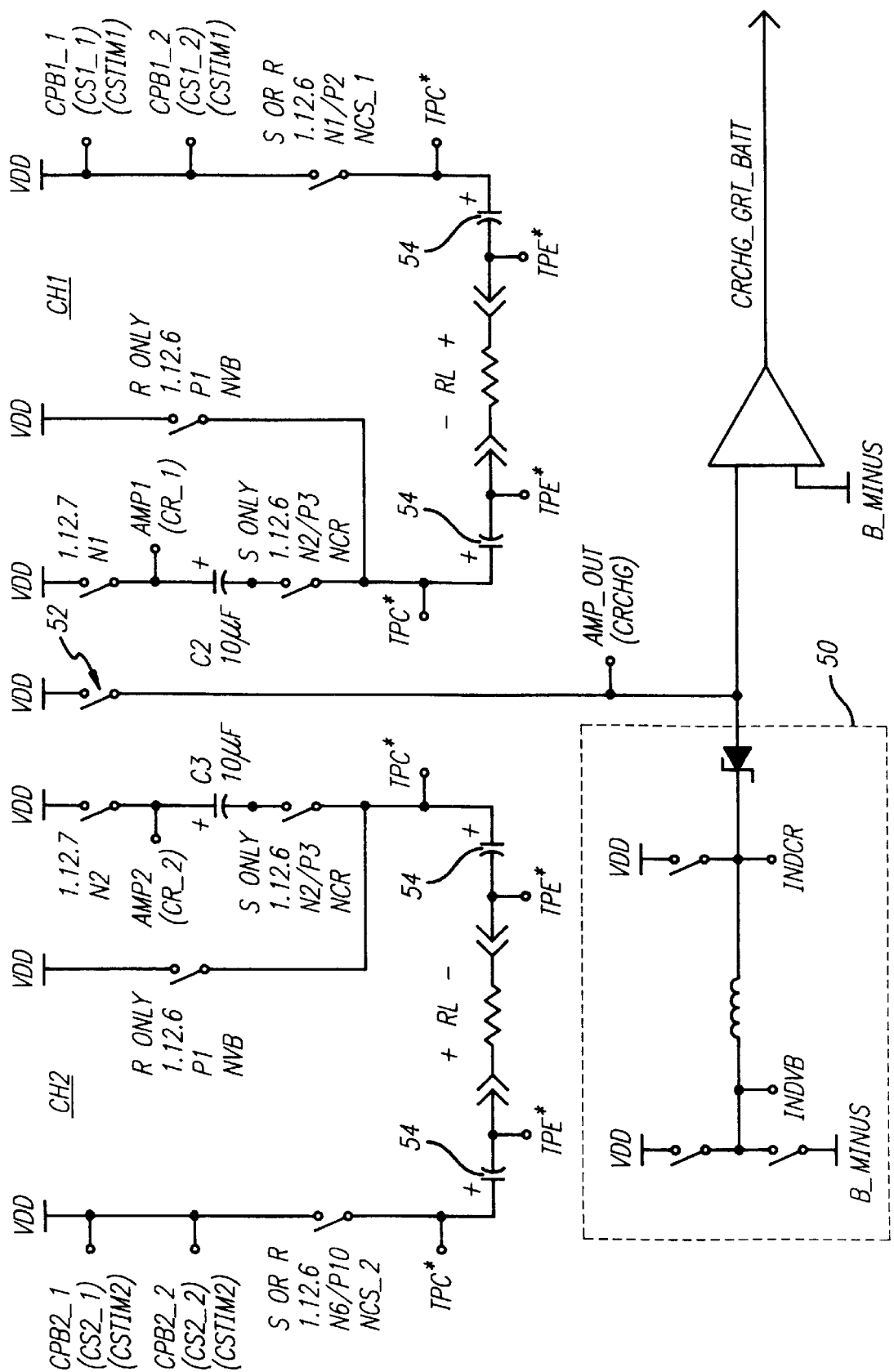
FIG. 9 depicts an idealistic representation of the dual channel ITREL ("DCI") version of the implantable pulse generator utilized in one of the preferred embodiments of the present invention.
Figure 10:
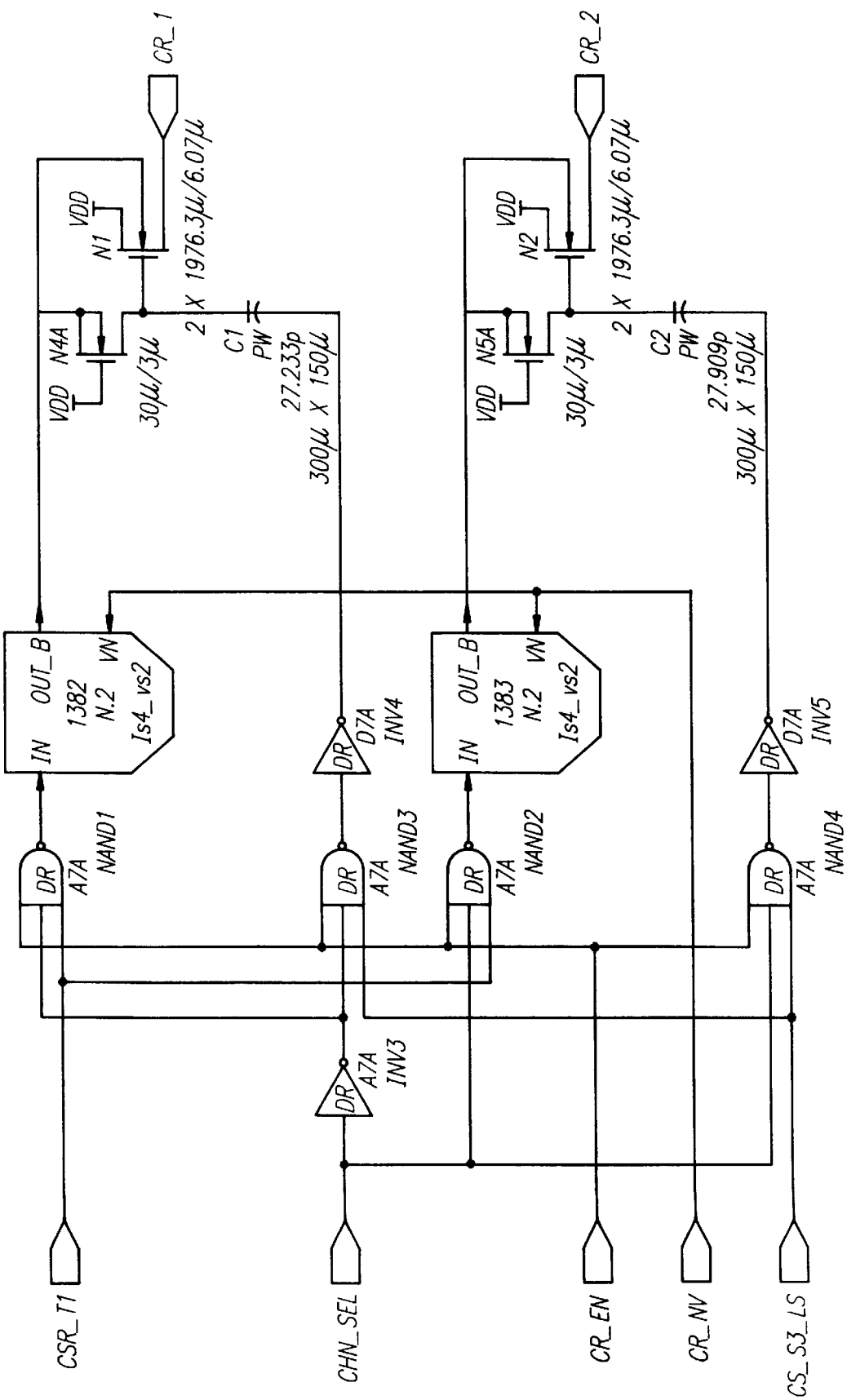
FIG. 10 shows the monolithic embodiment of switches N1 and N2 of FIG. 9 along with the additional circuitry required to actuate or toggle each switch into the closed or open position.
Figure 11A:
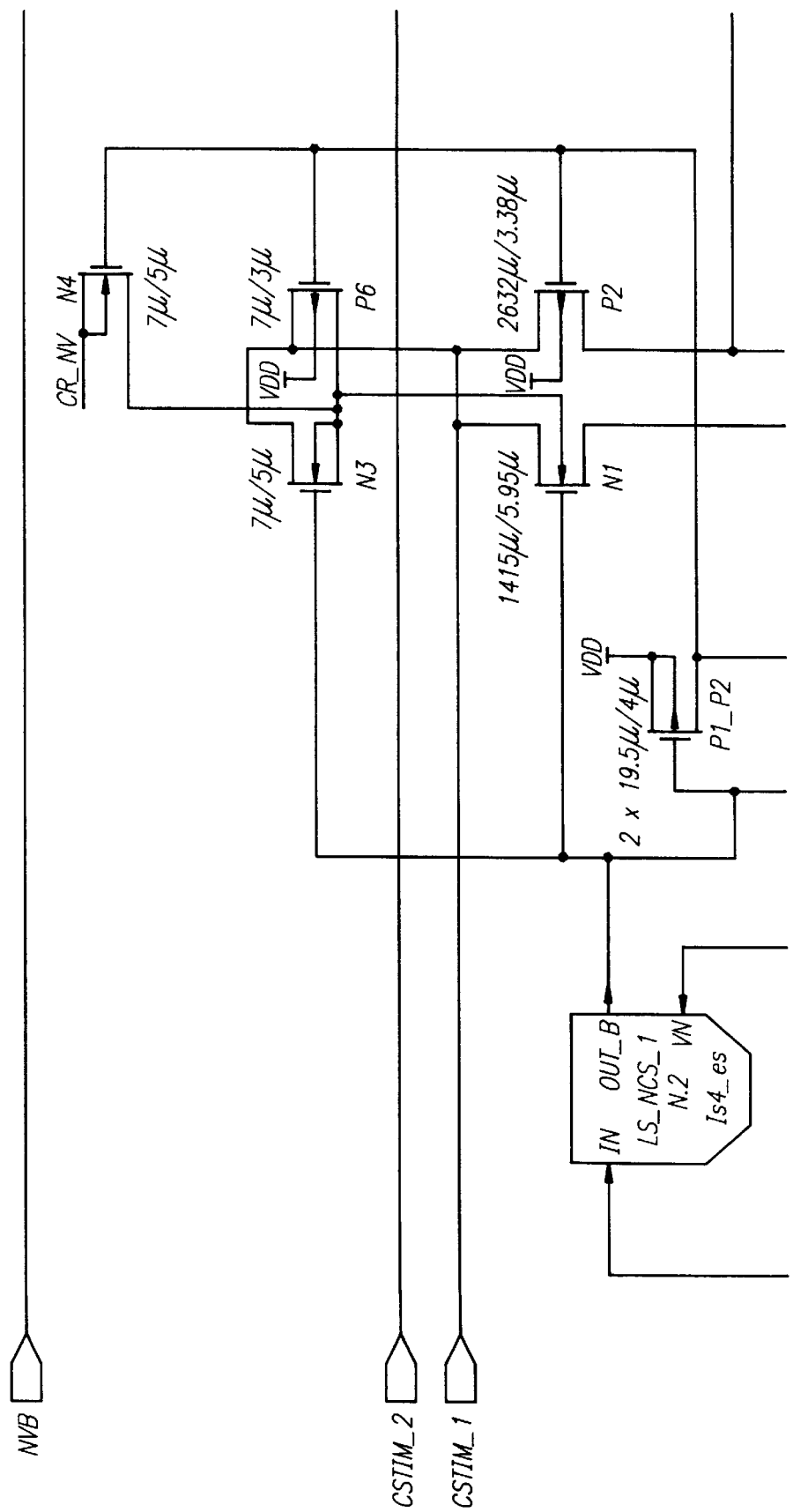
FIGS. 11A–11D are a schematic of the electrode switch utilized in each stimulating ("S"), recharging ("R"), and stimulating or recharging ("S or R") switch depicted in FIG. 9.
Figure 11B:
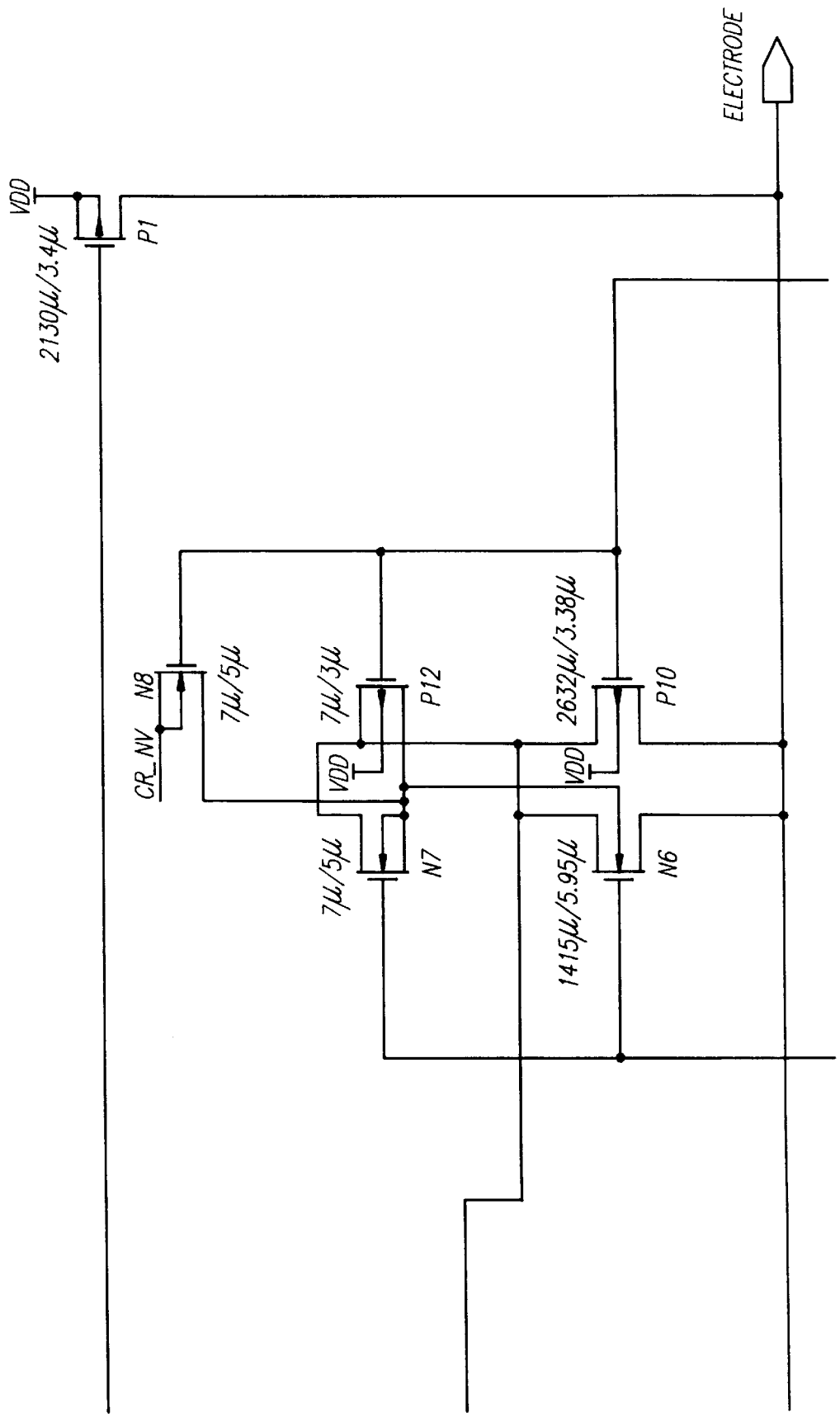
Figure 11C:
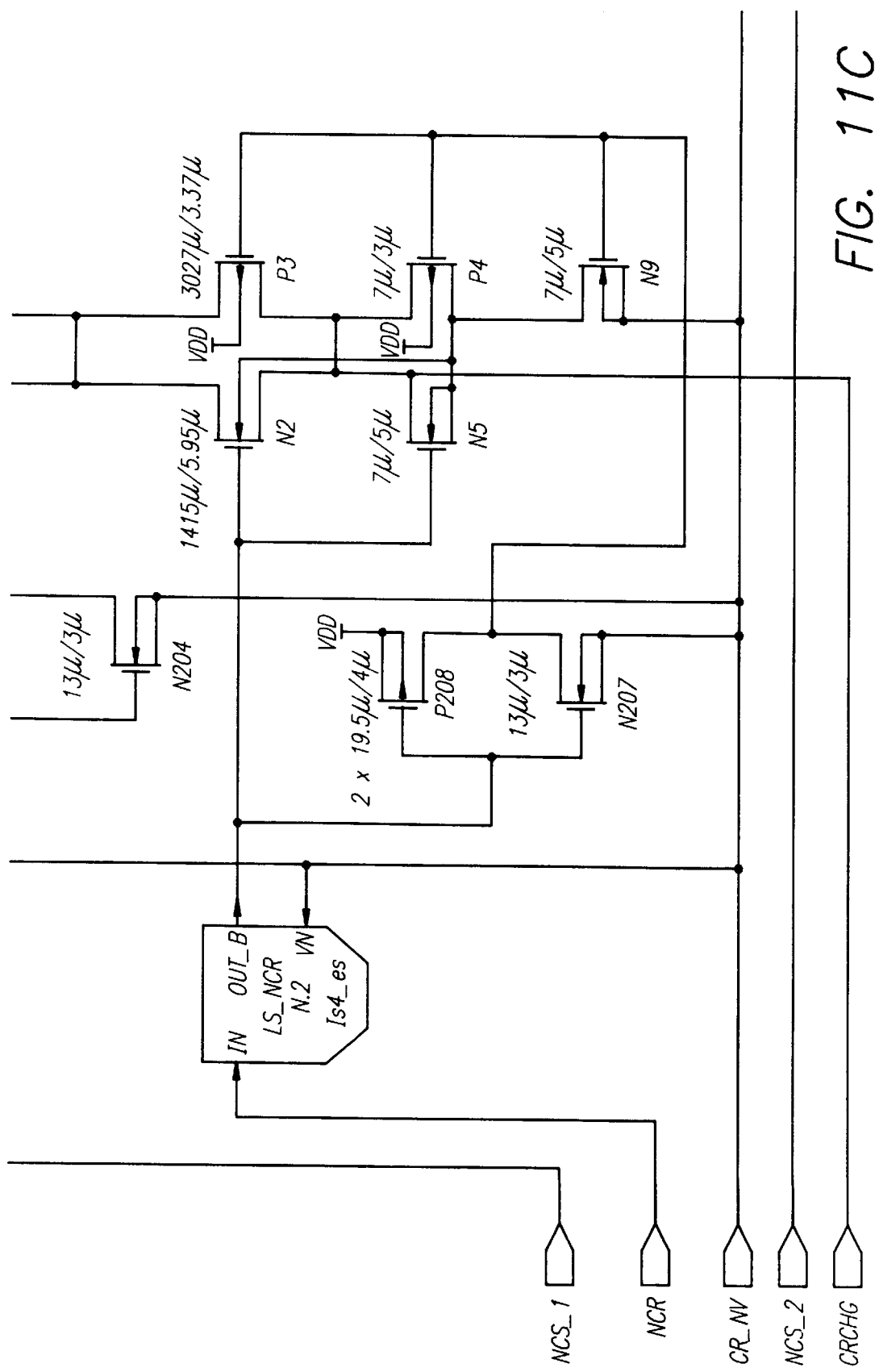
Figure 11D:
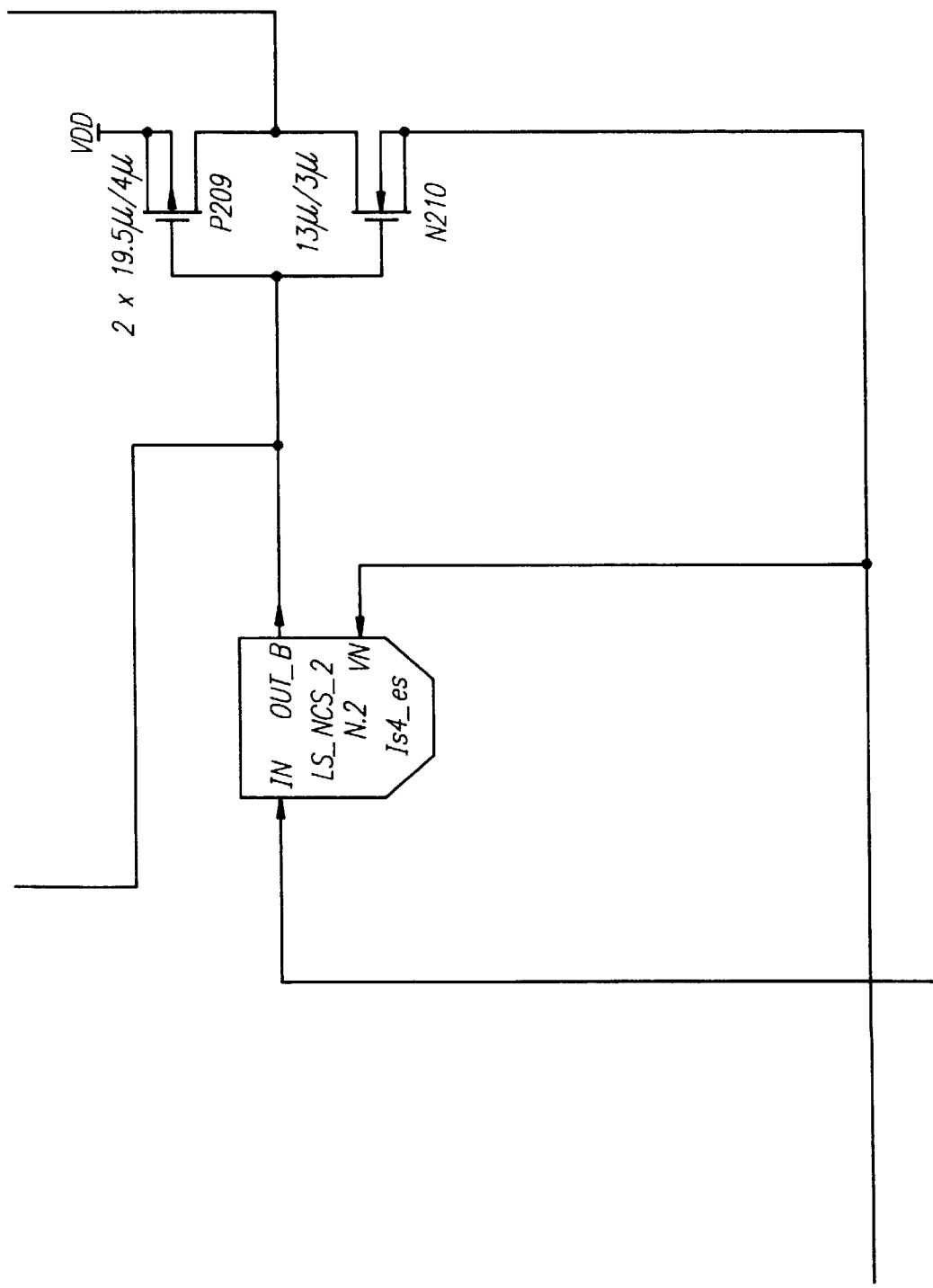
Figure 12:
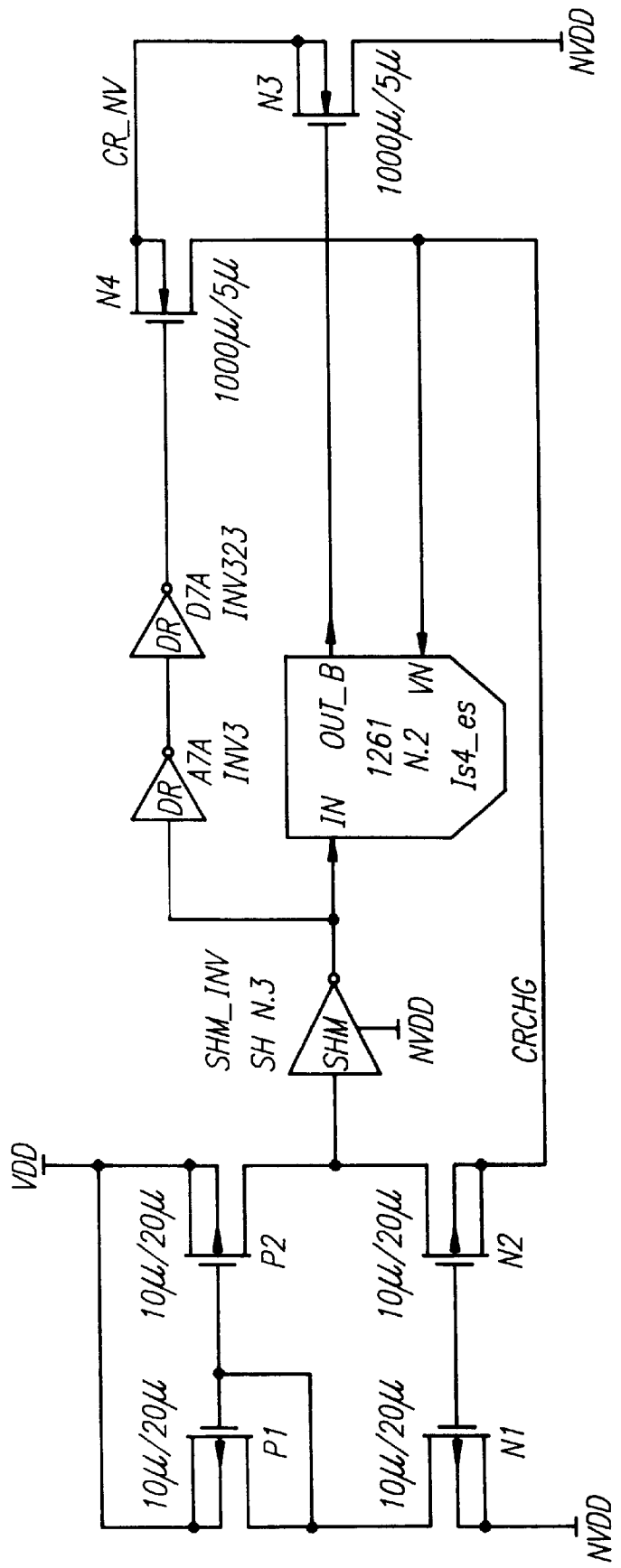
FIG. 12 is a schematic of the circuit used to identify the most negative reference that is utilized as the AMP_OUT voltage level of FIG. 9.
Figure 13:
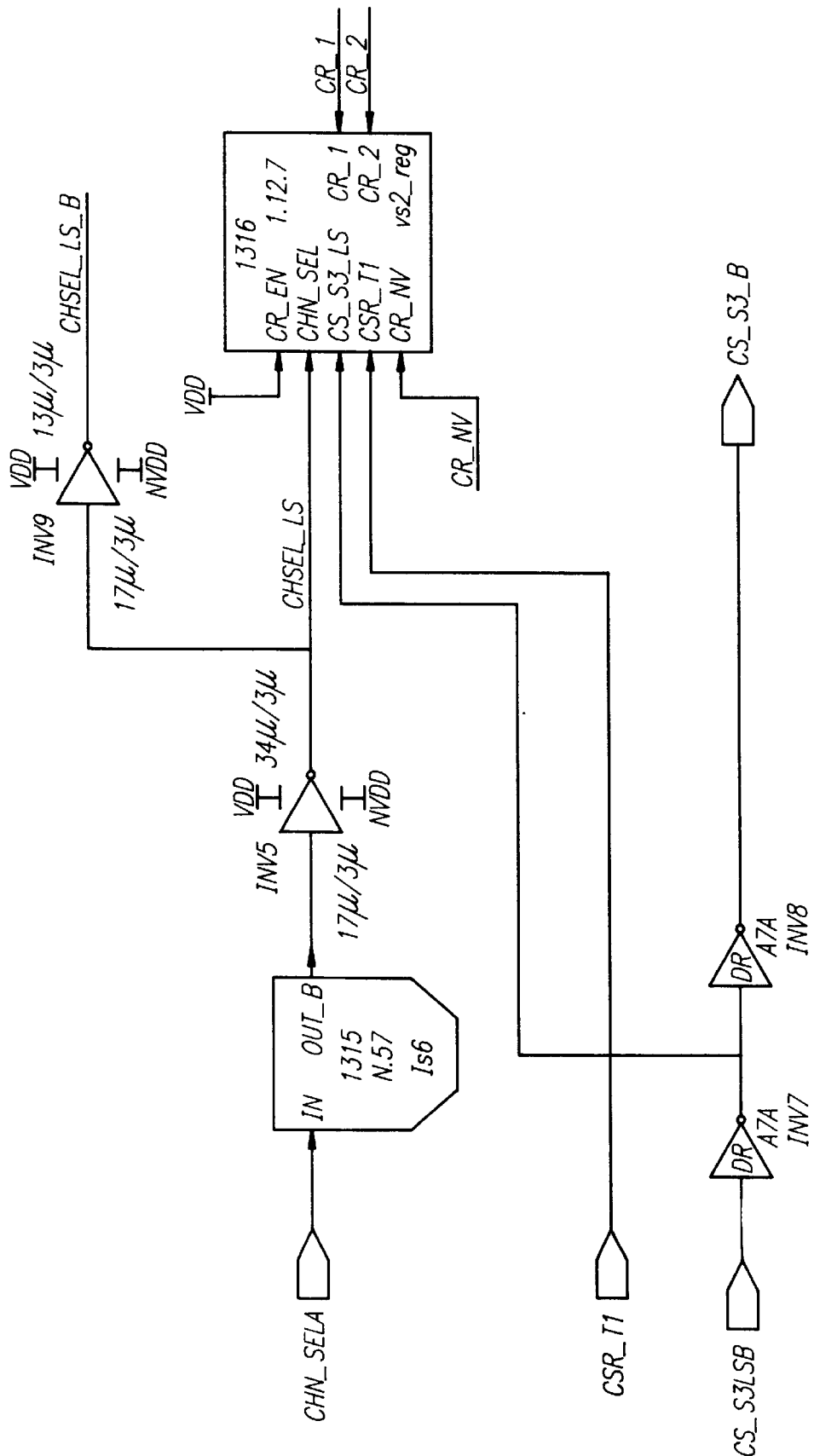
FIGS. 13 and 14A–14E illustrate the top level representation—along with the relevant control signals driving the electrode switches—of the output circuit depicted in FIG. 9.
Figure 14A:
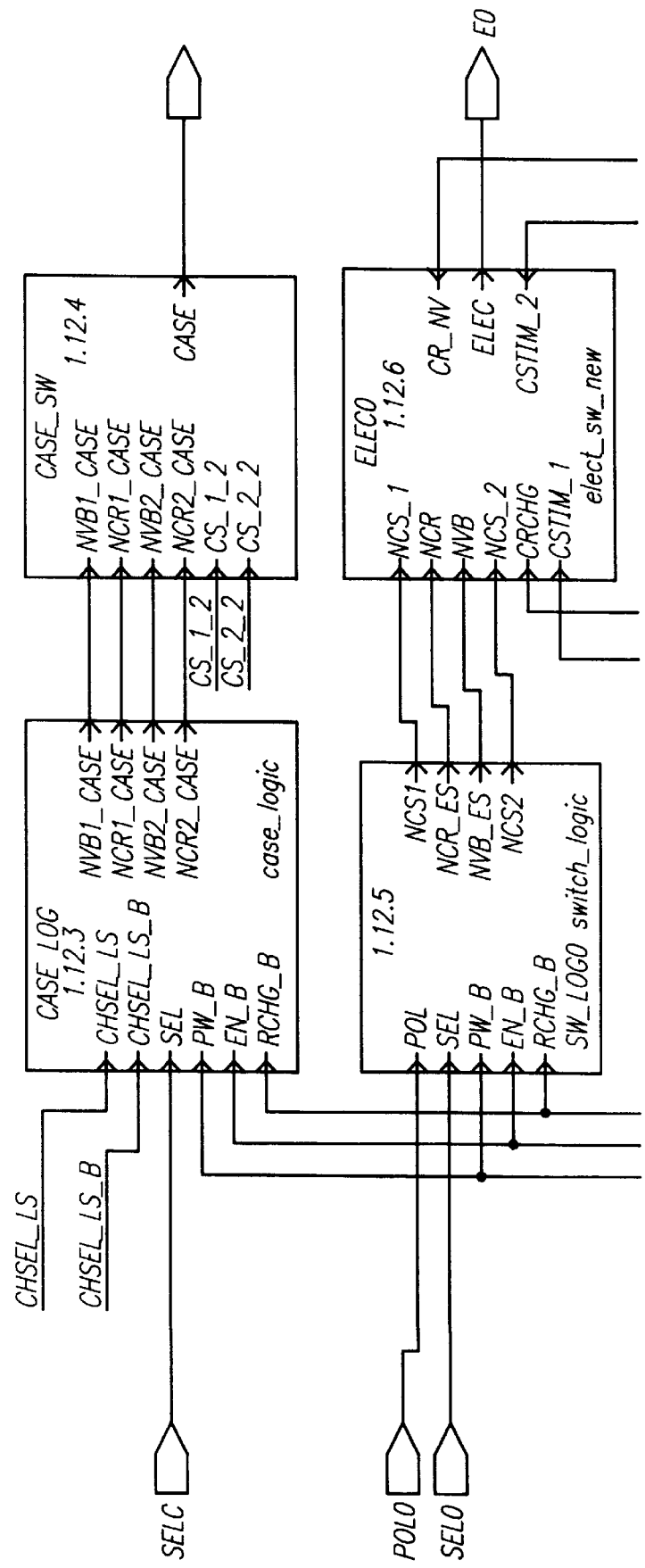
Figure 14B:
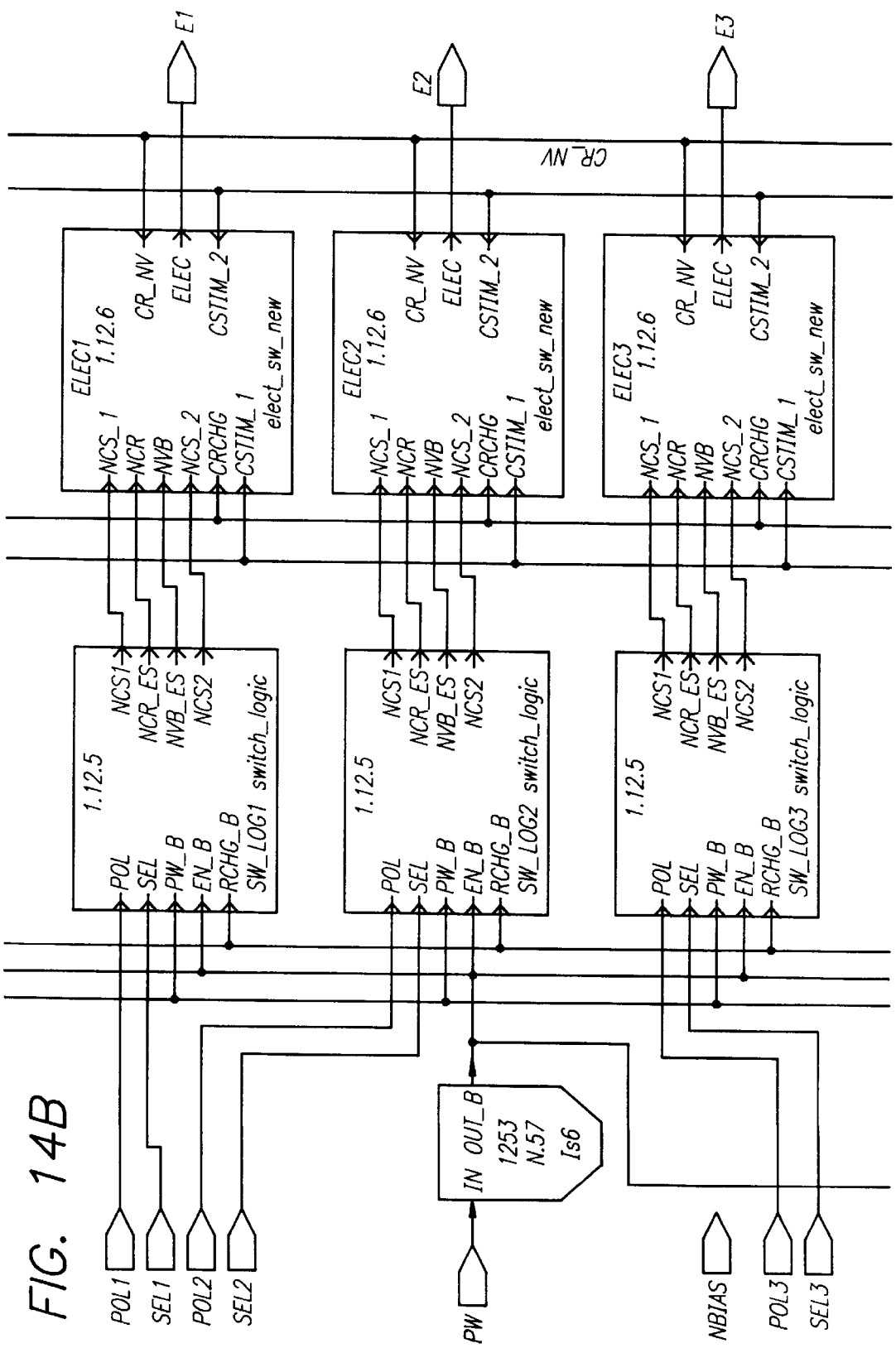
Figure 14C:
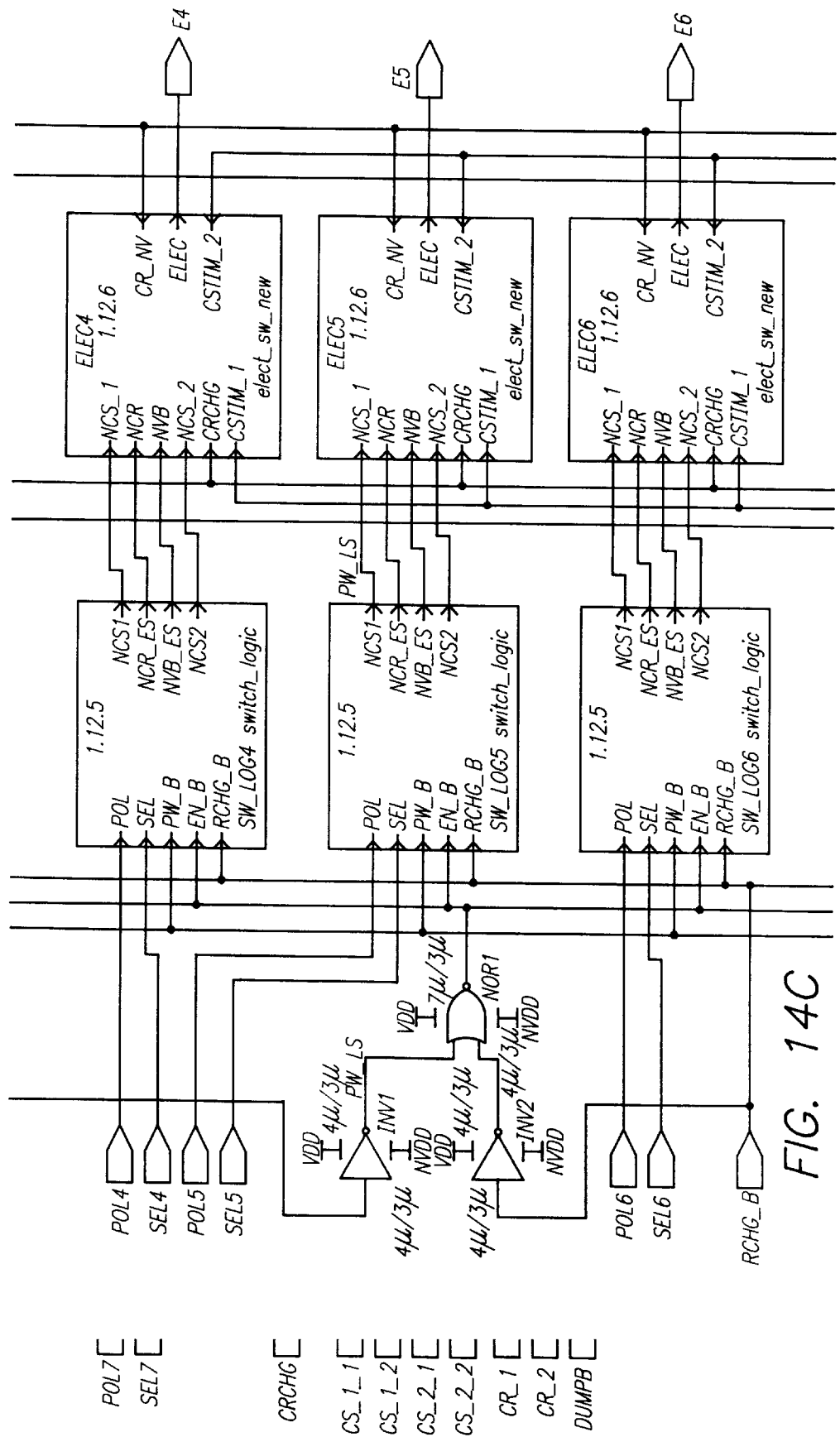
Figure 14D:
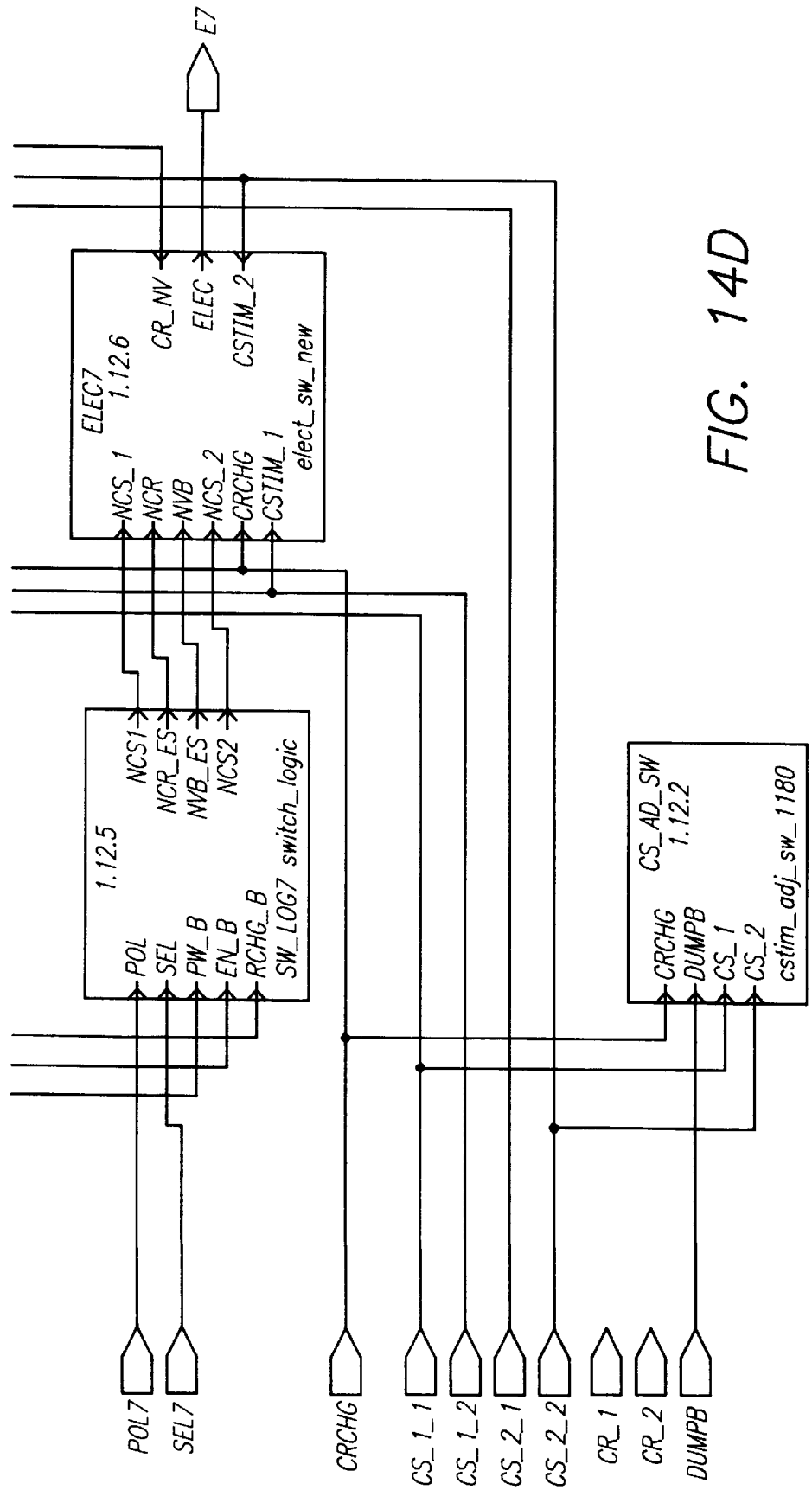
Figure 14E:
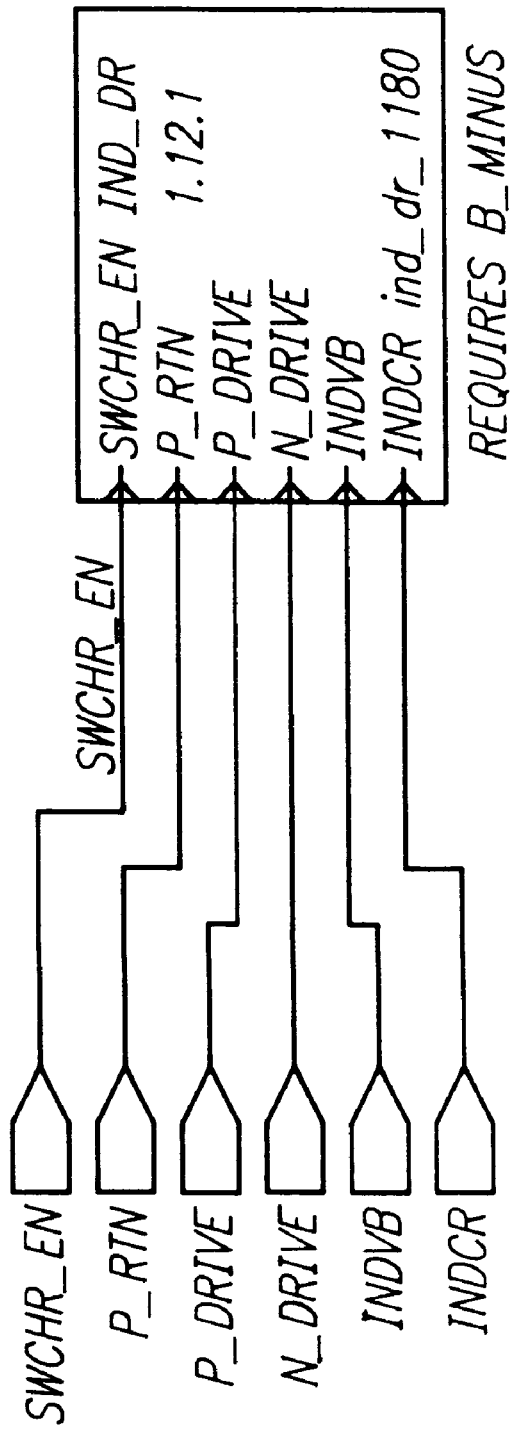
Figures 15, 15A:
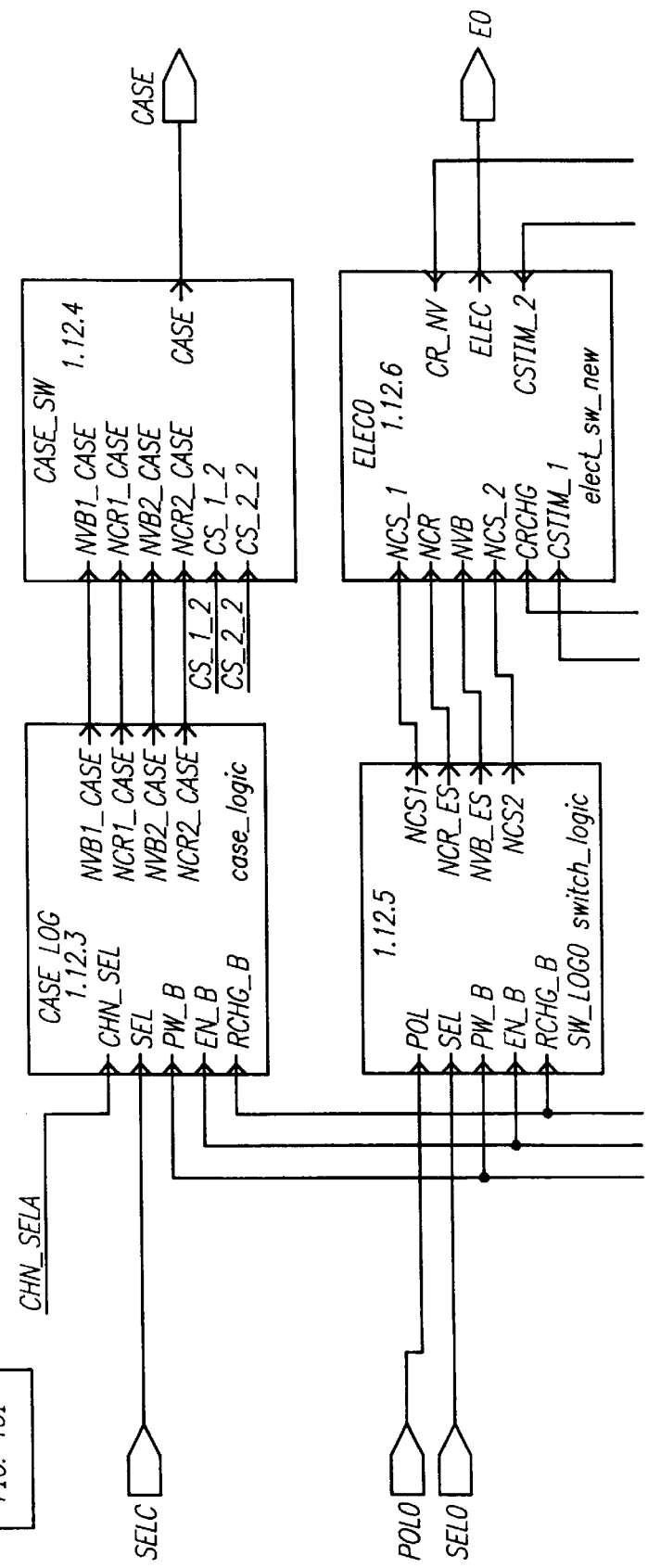
FIGS. 15 and 15A–15I illustrate an output control circuit for an alternative implantable pulse generator output circuit capable of producing a 'transverse tripolar stimulation'.
Figure 15B:
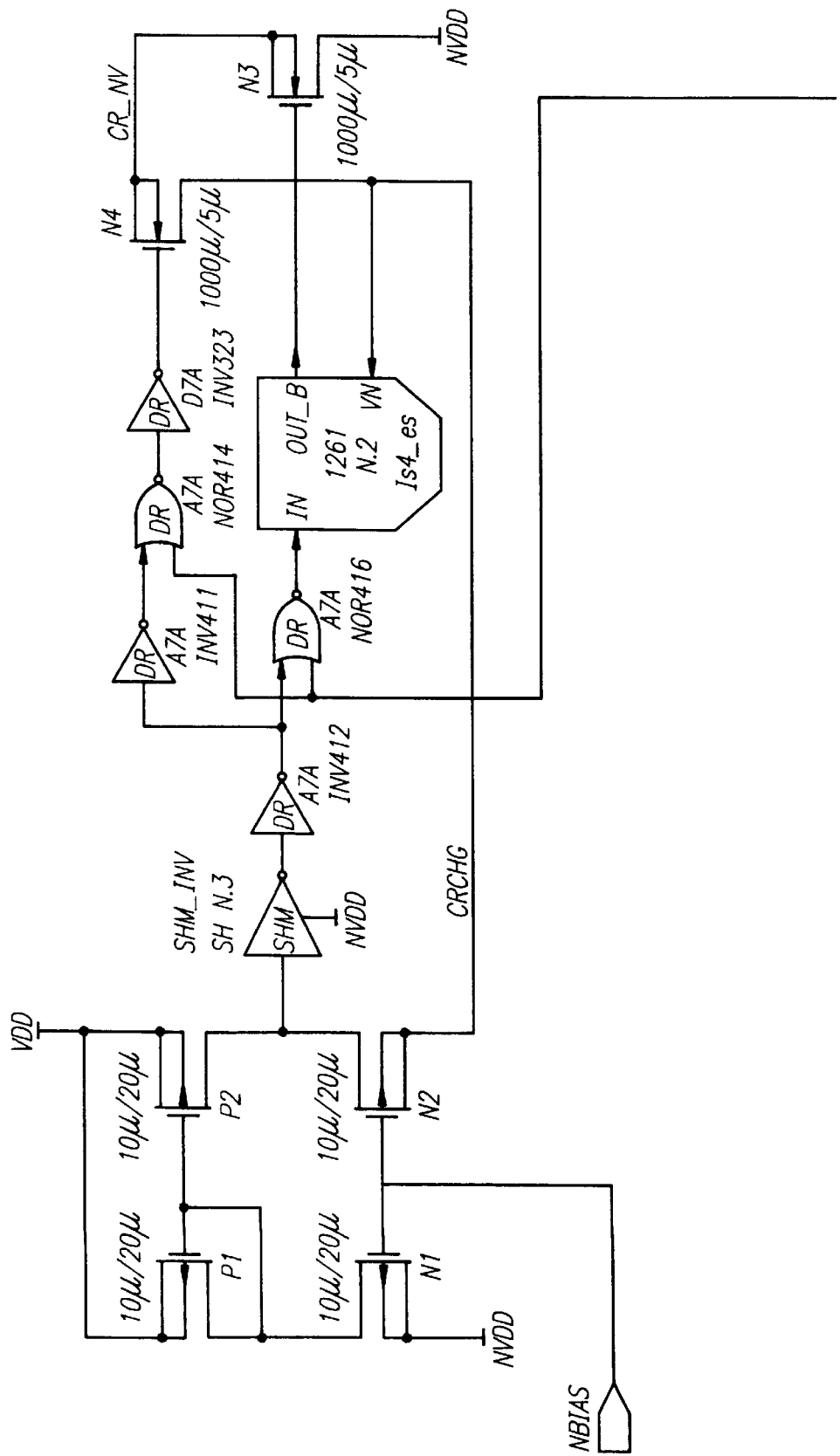
Figure 15C:
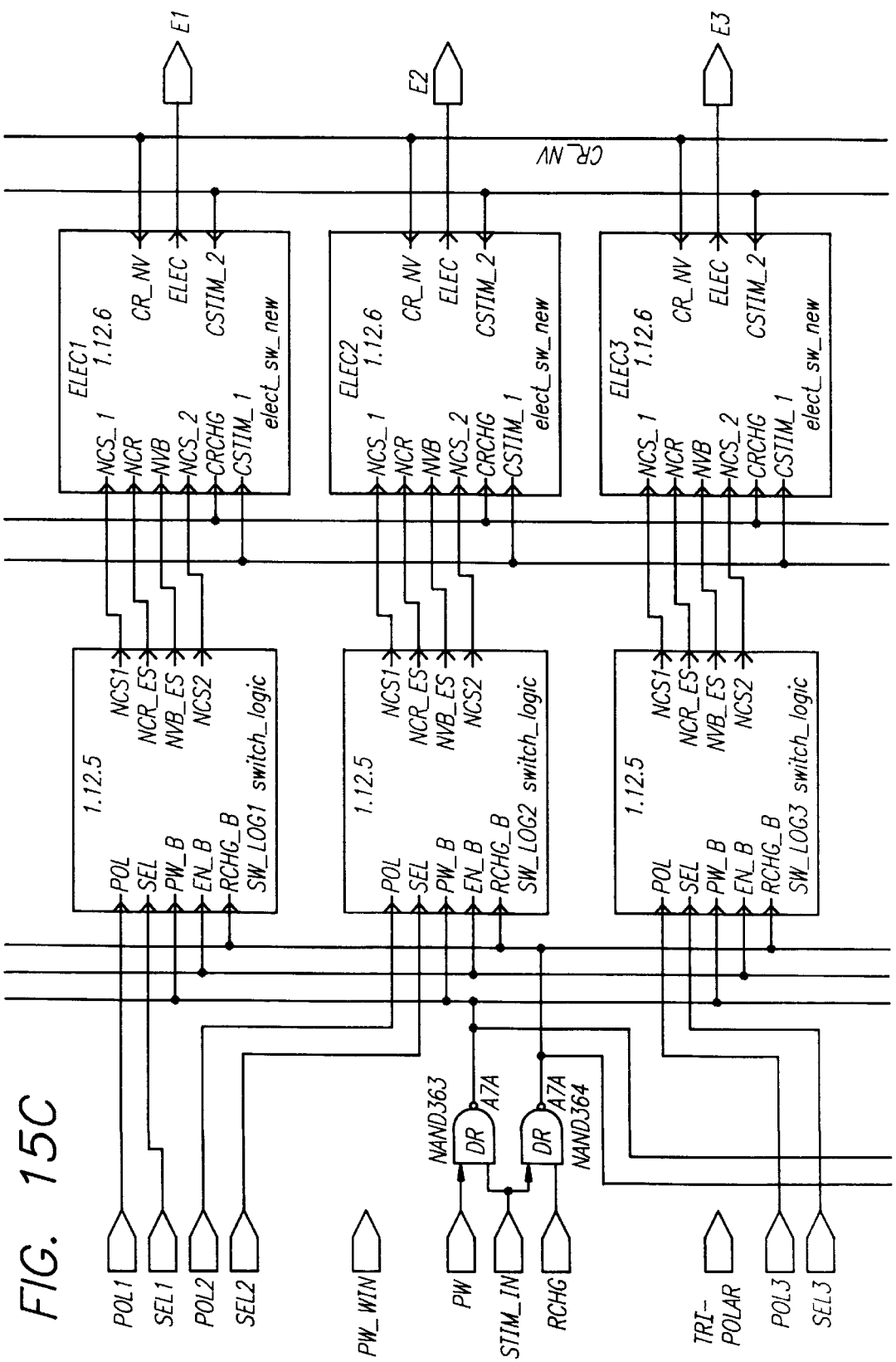
Figure 15D:
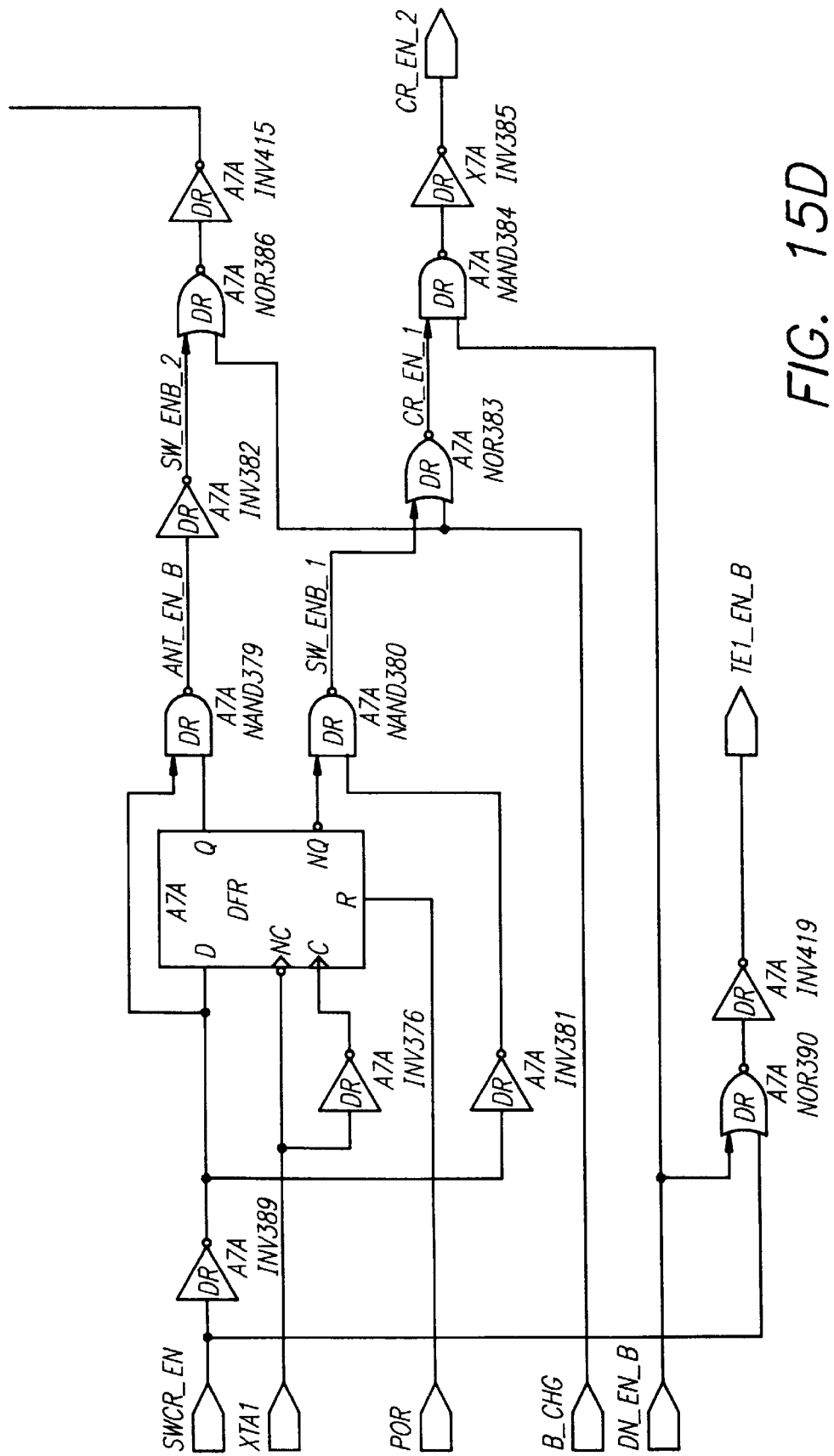
Figure 15E:
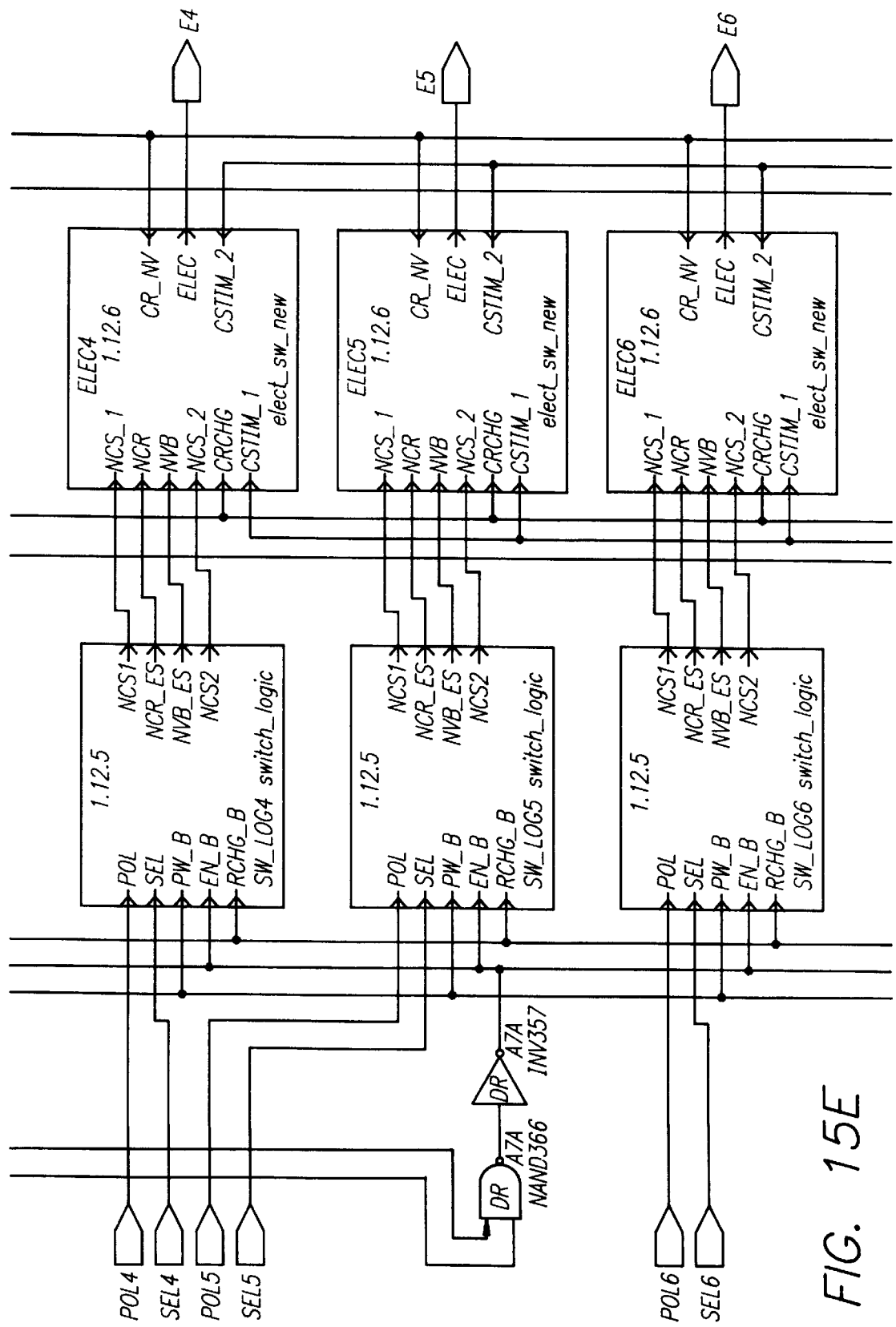
Figure 15F:
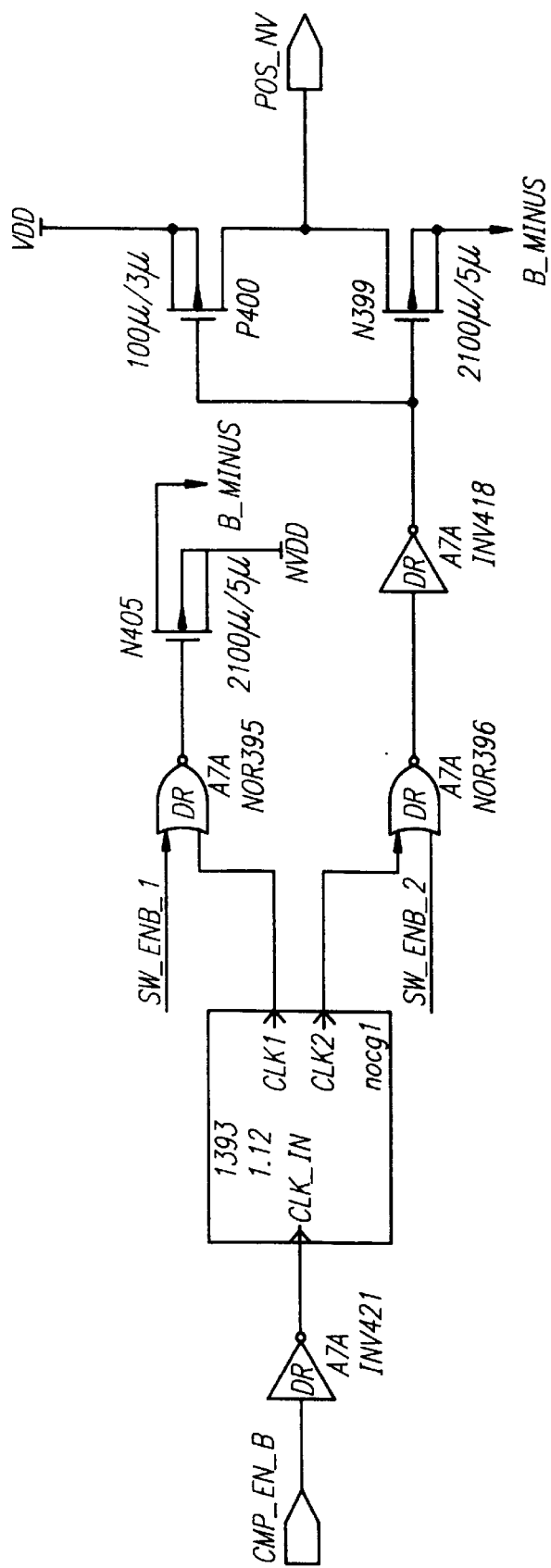
Figure 15G:
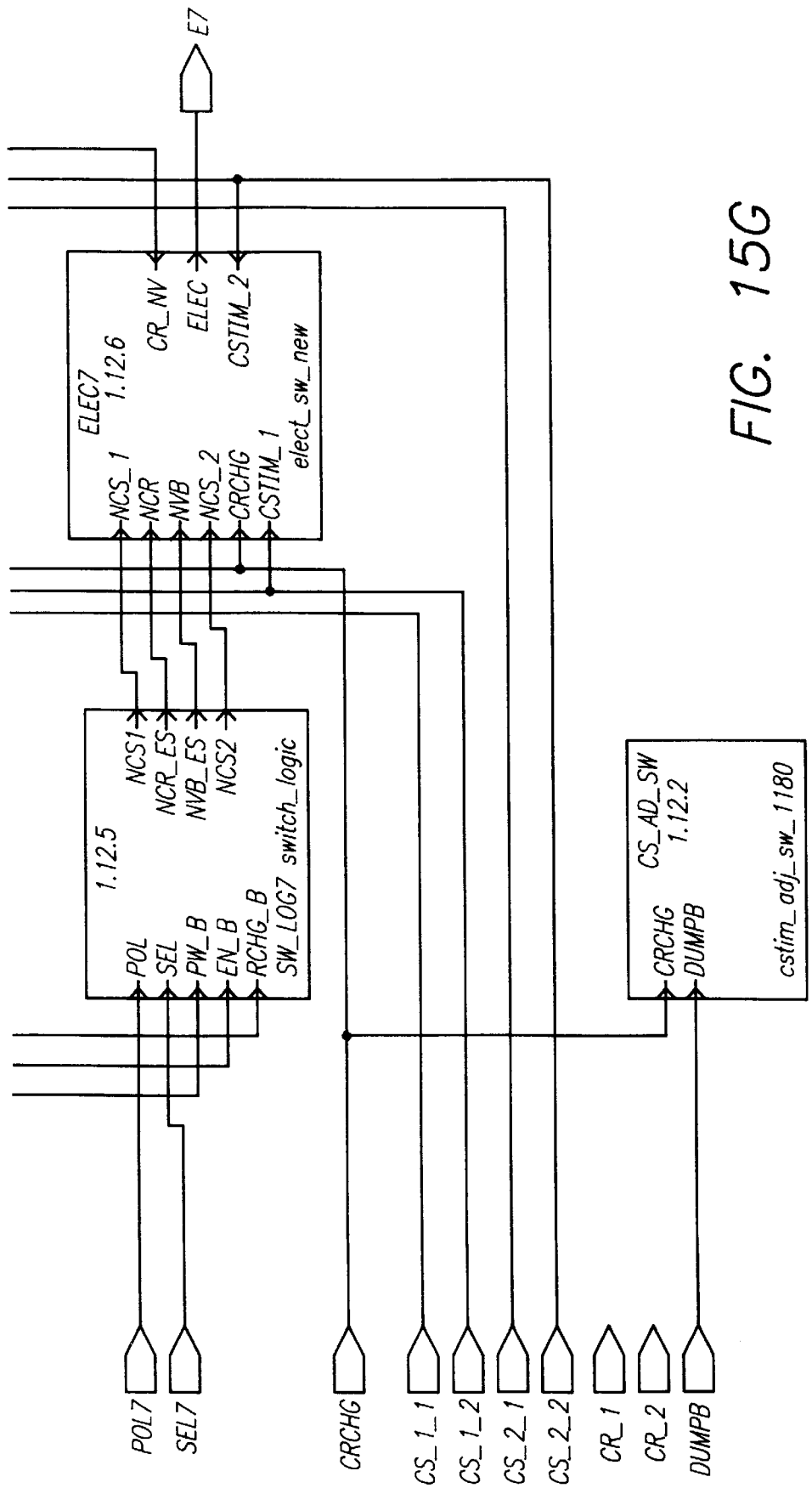
Figure 15H:
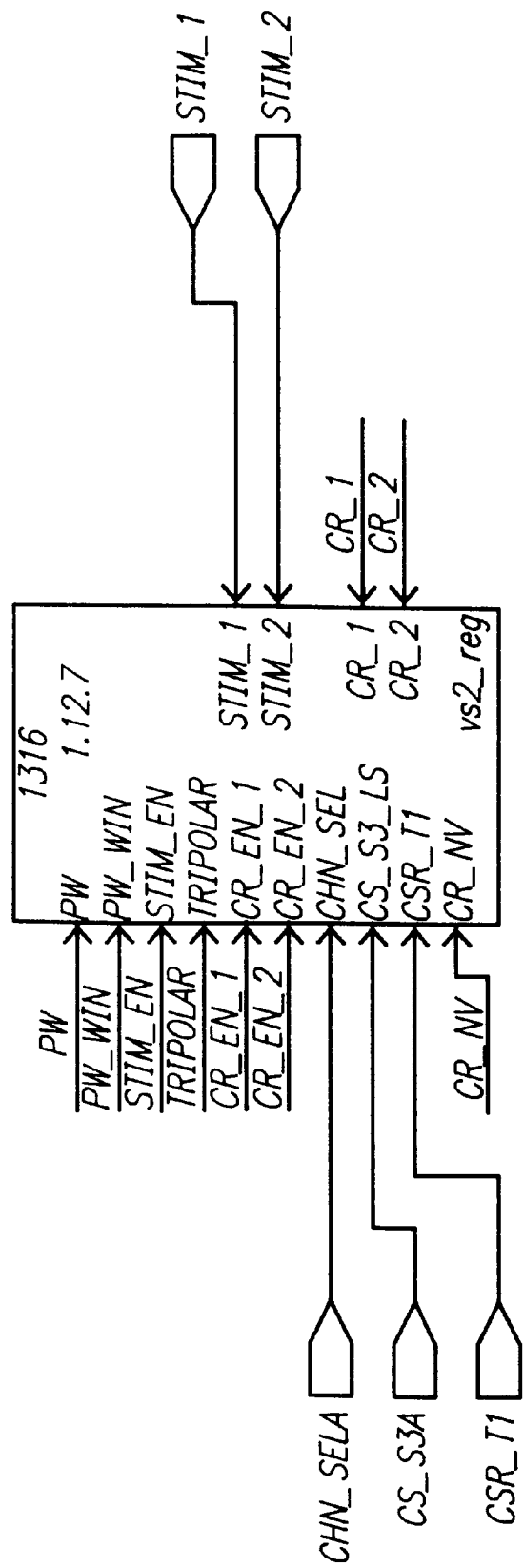
Figure 15I:
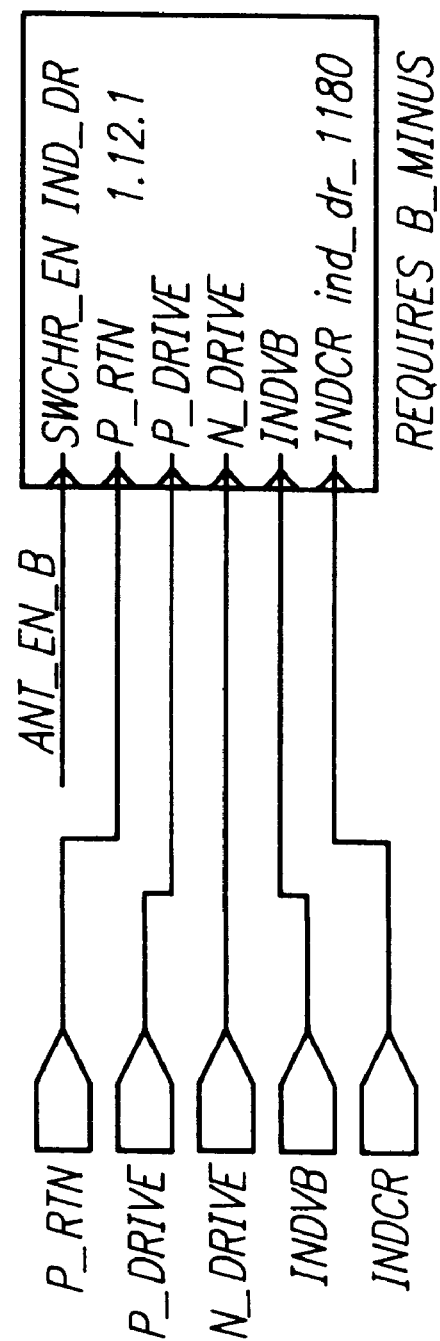
Figure 16A:
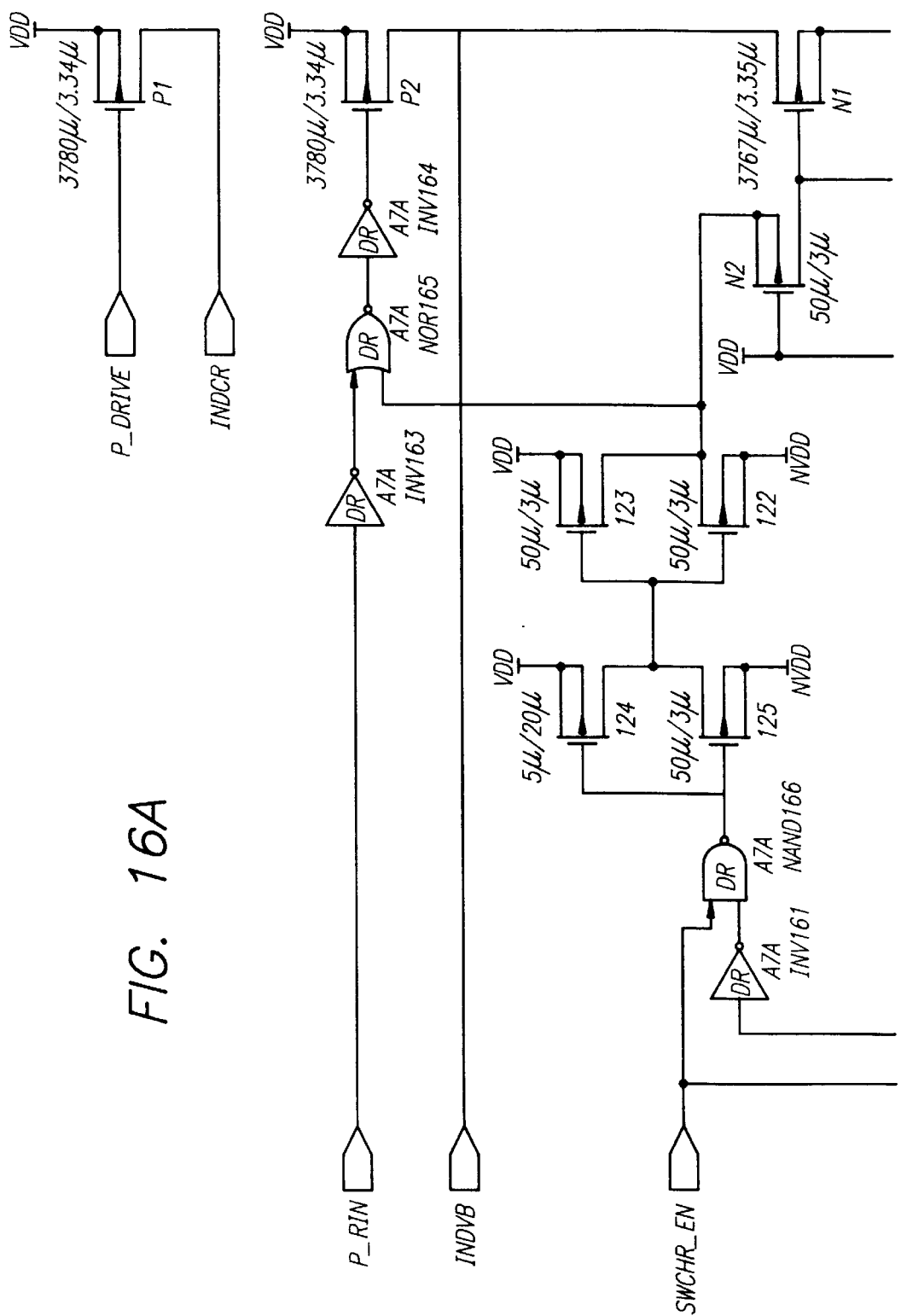
FIGS. 16A–16B illustrate a circuit used to identify the most negative reference voltage used by the output circuit of FIGS. 15 and 15A–15I.
Figure 16B:
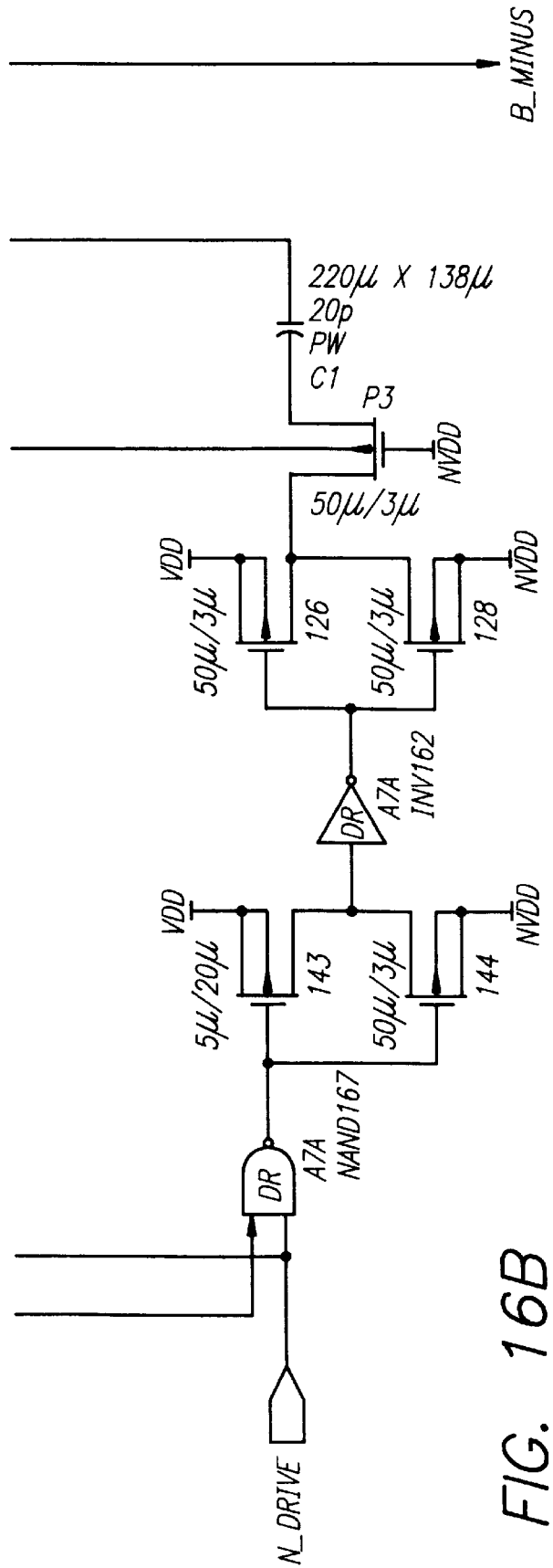
Figure 17:
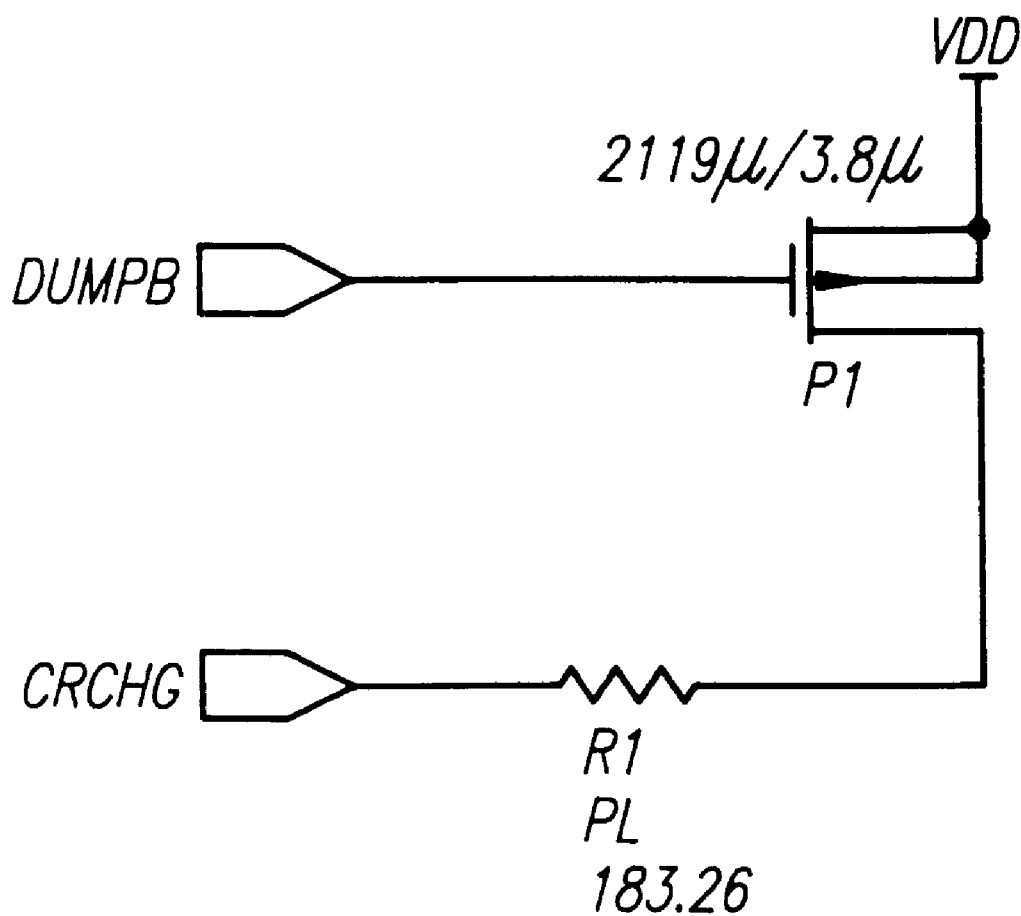
FIGS. 17–20 illustrate the control circuits for controlling switches NCS_1 and NCS_2 as shown in FIG. 9 to produce the alternative 'transverse tripolar stimulation' associated with the circuitry of FIGS. 15 and 15A–15I.
Figure 18:
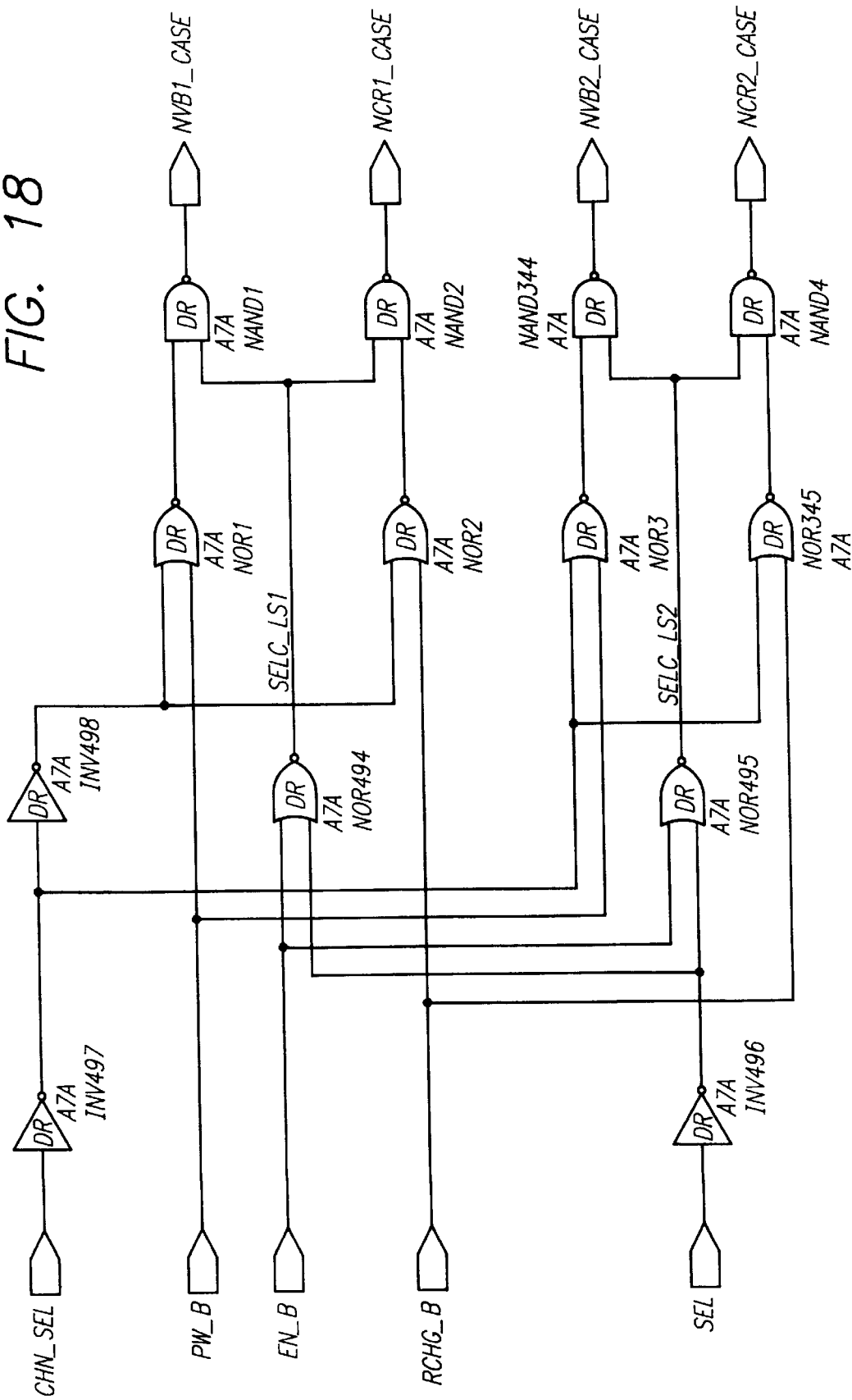
Figure 19:
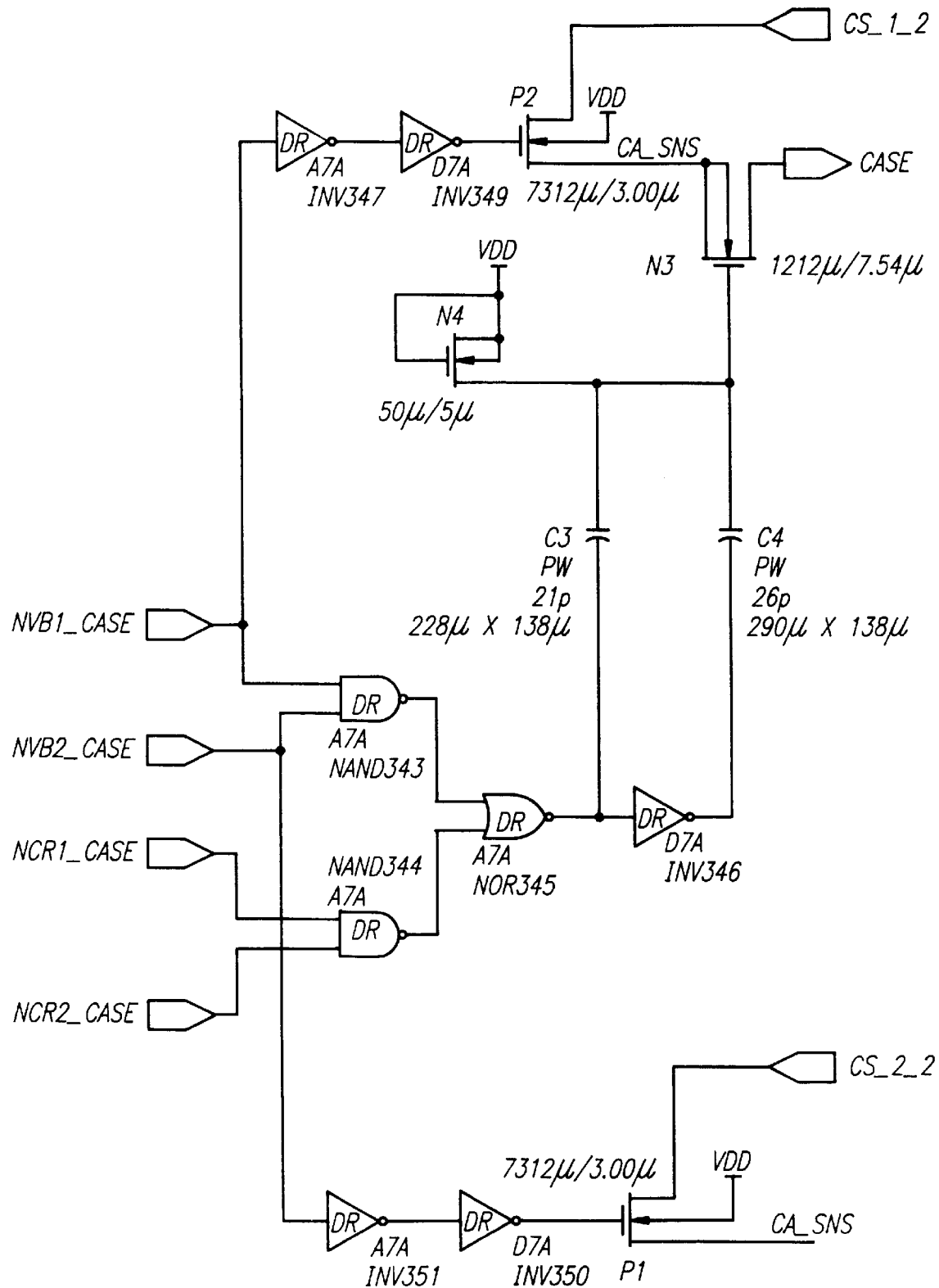
Figure 20:
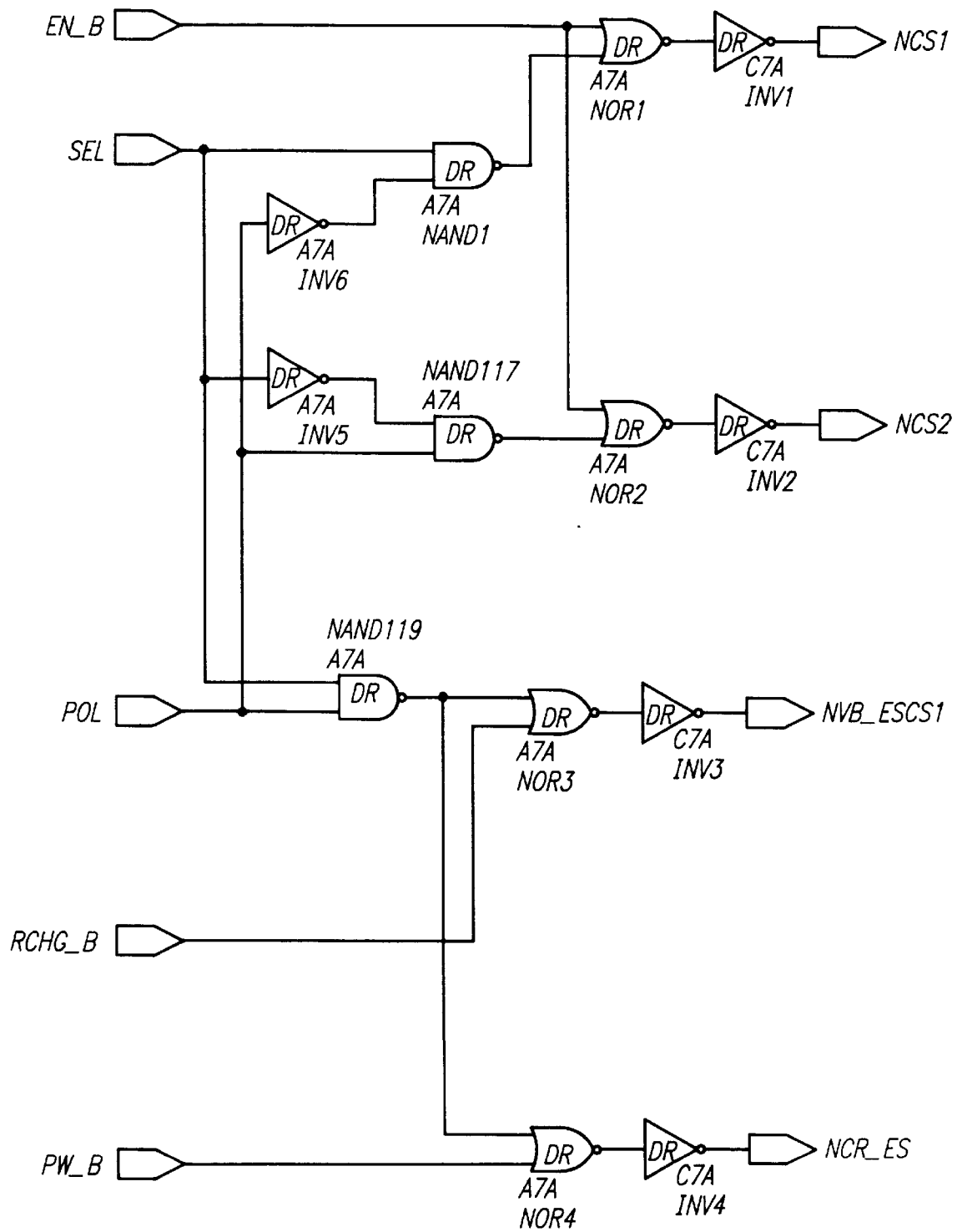
Figure 21A:
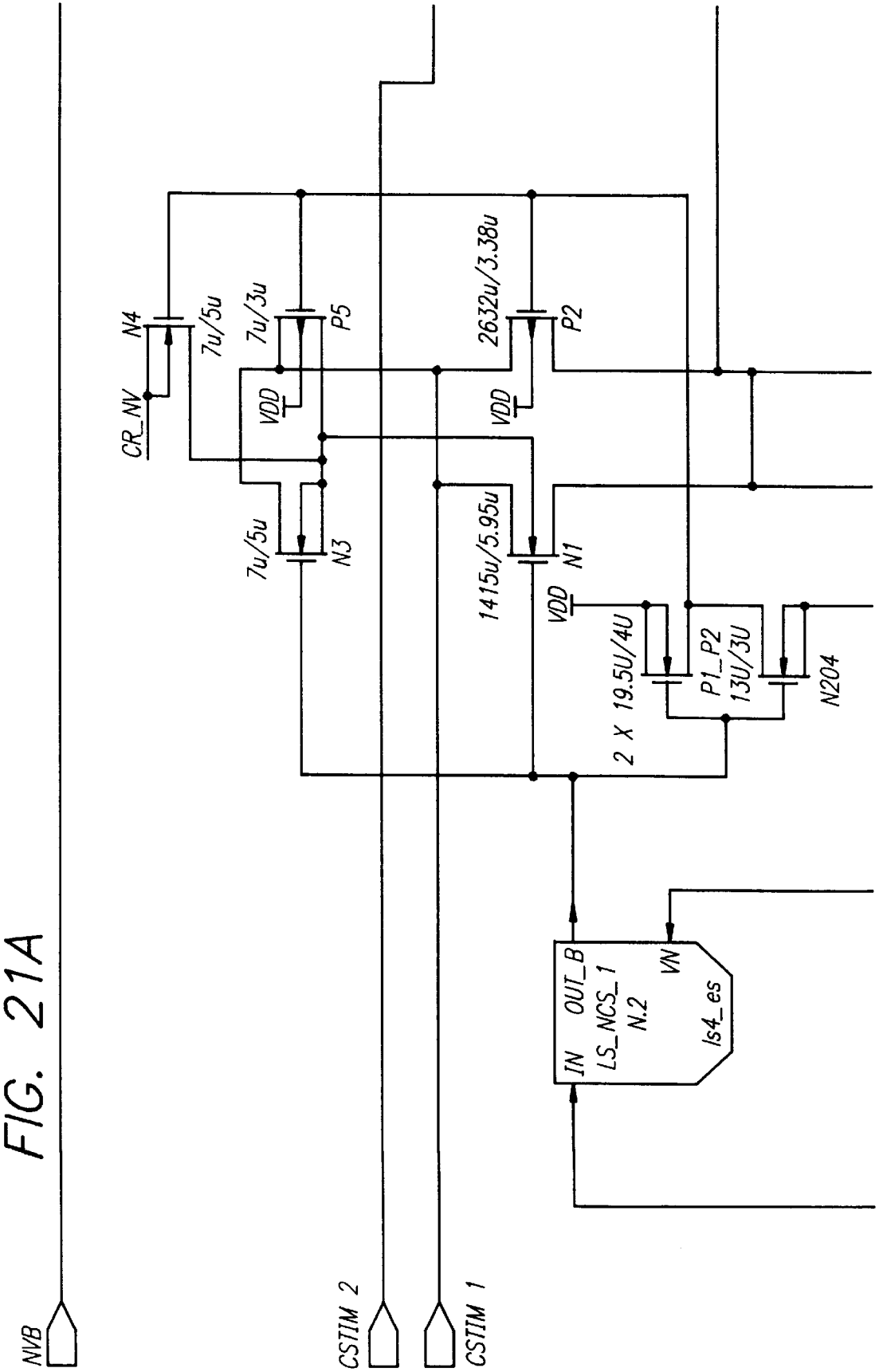
Figure 21B:
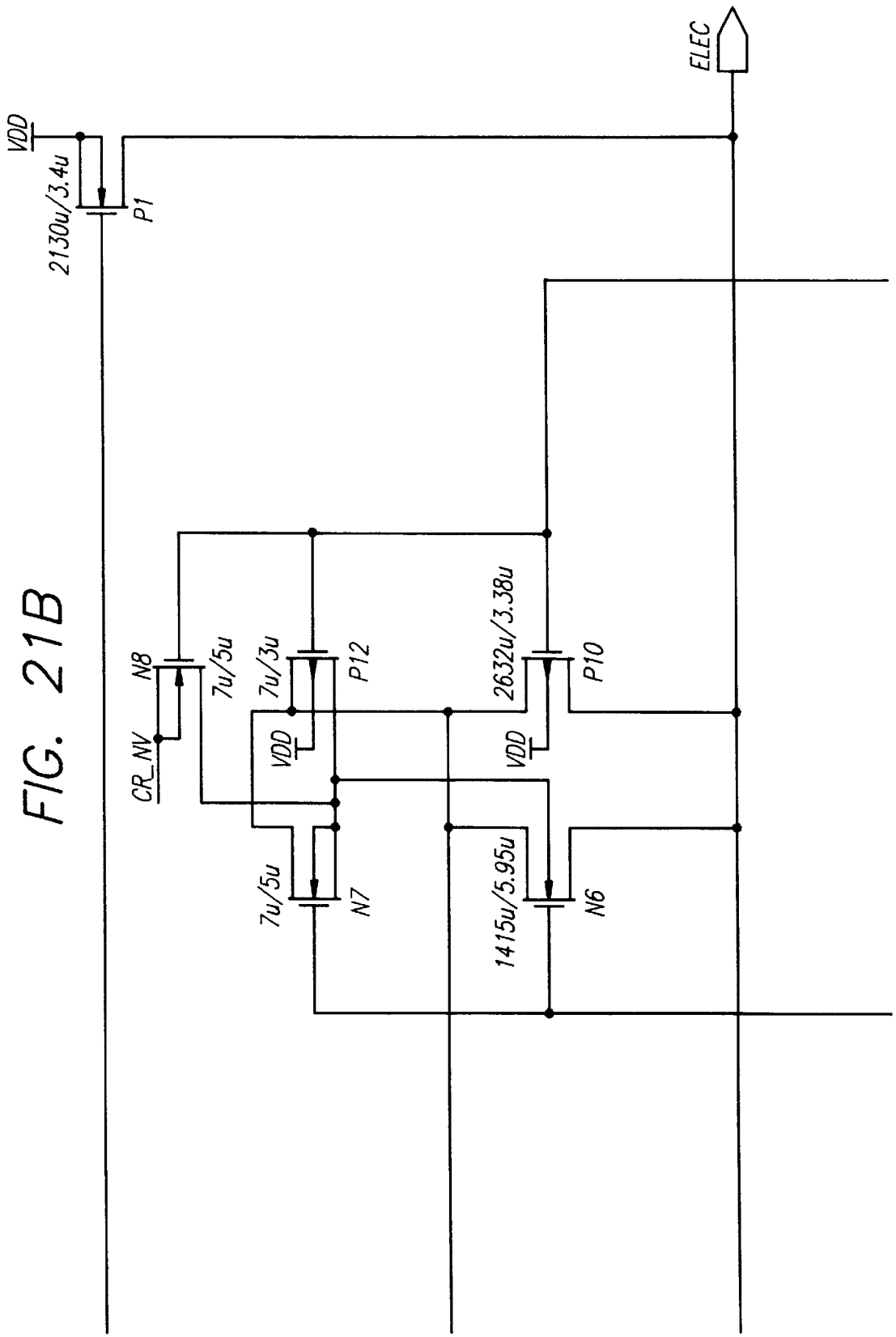
Figure 21D:
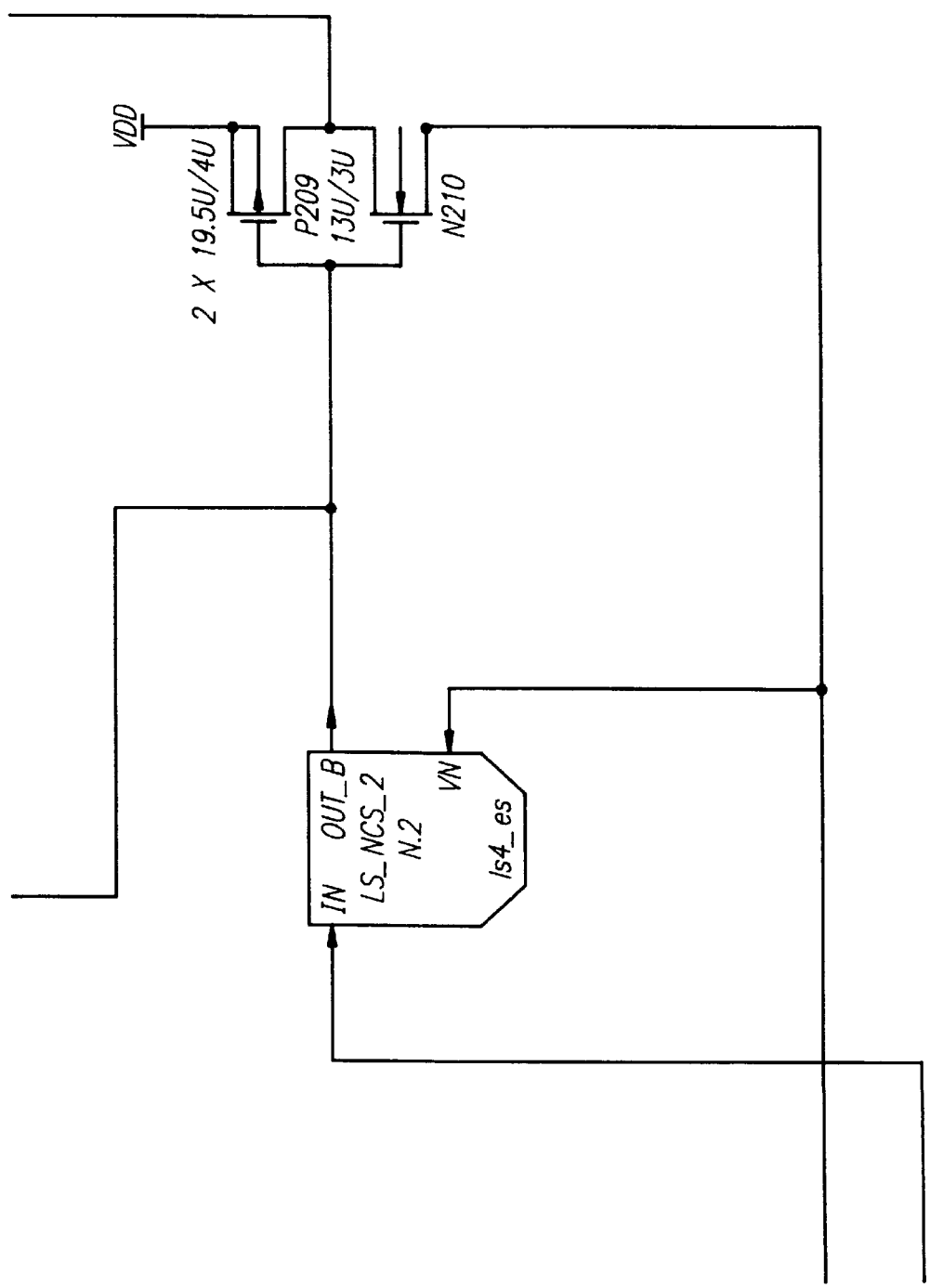
Figure 22A:
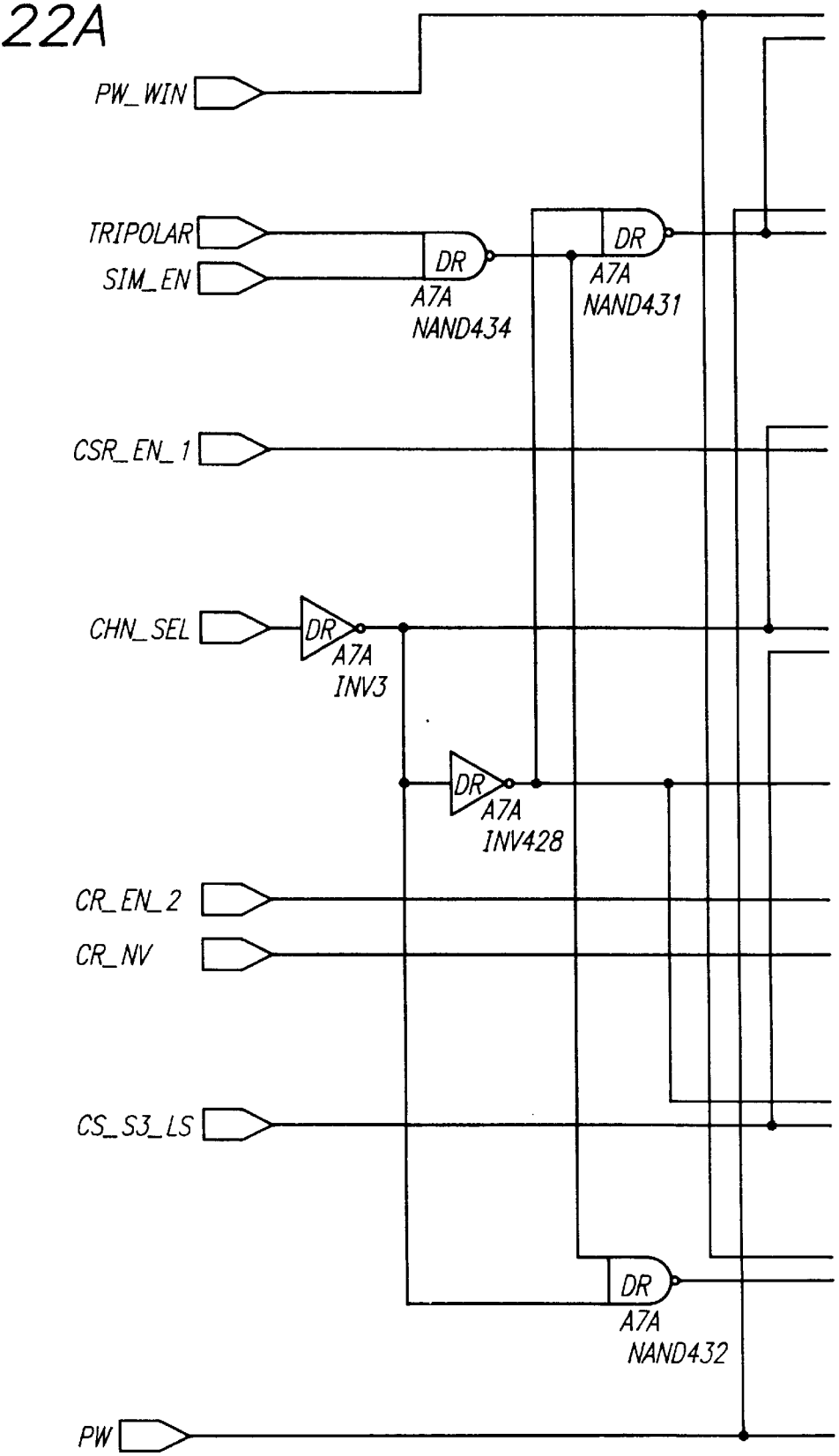
FIGS. 22A–22C illustrate additional output control circuits associated with the embodiment of FIGS. 15 and 15A–15I.
Figure 22B:
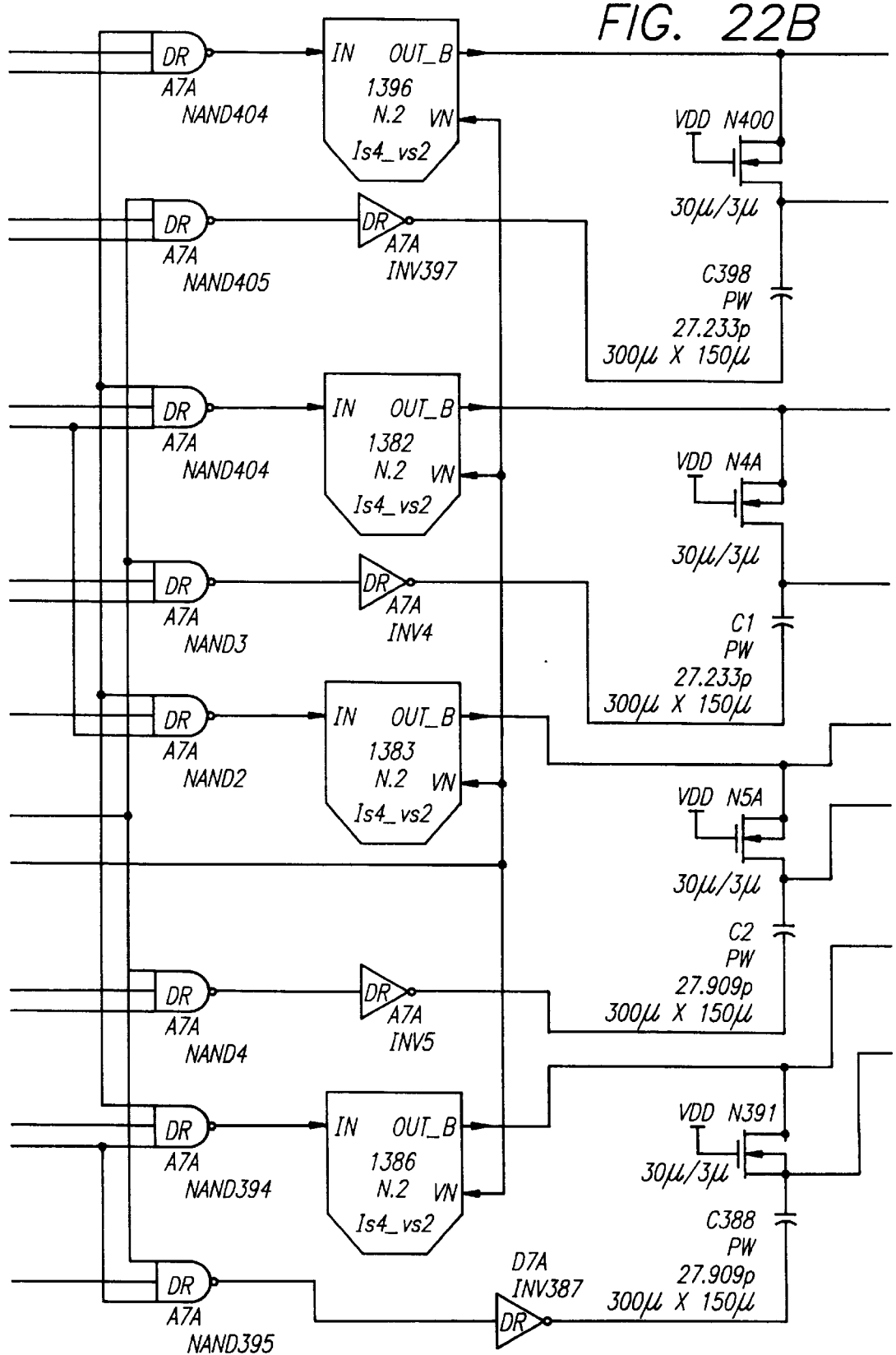
Figure 22C:
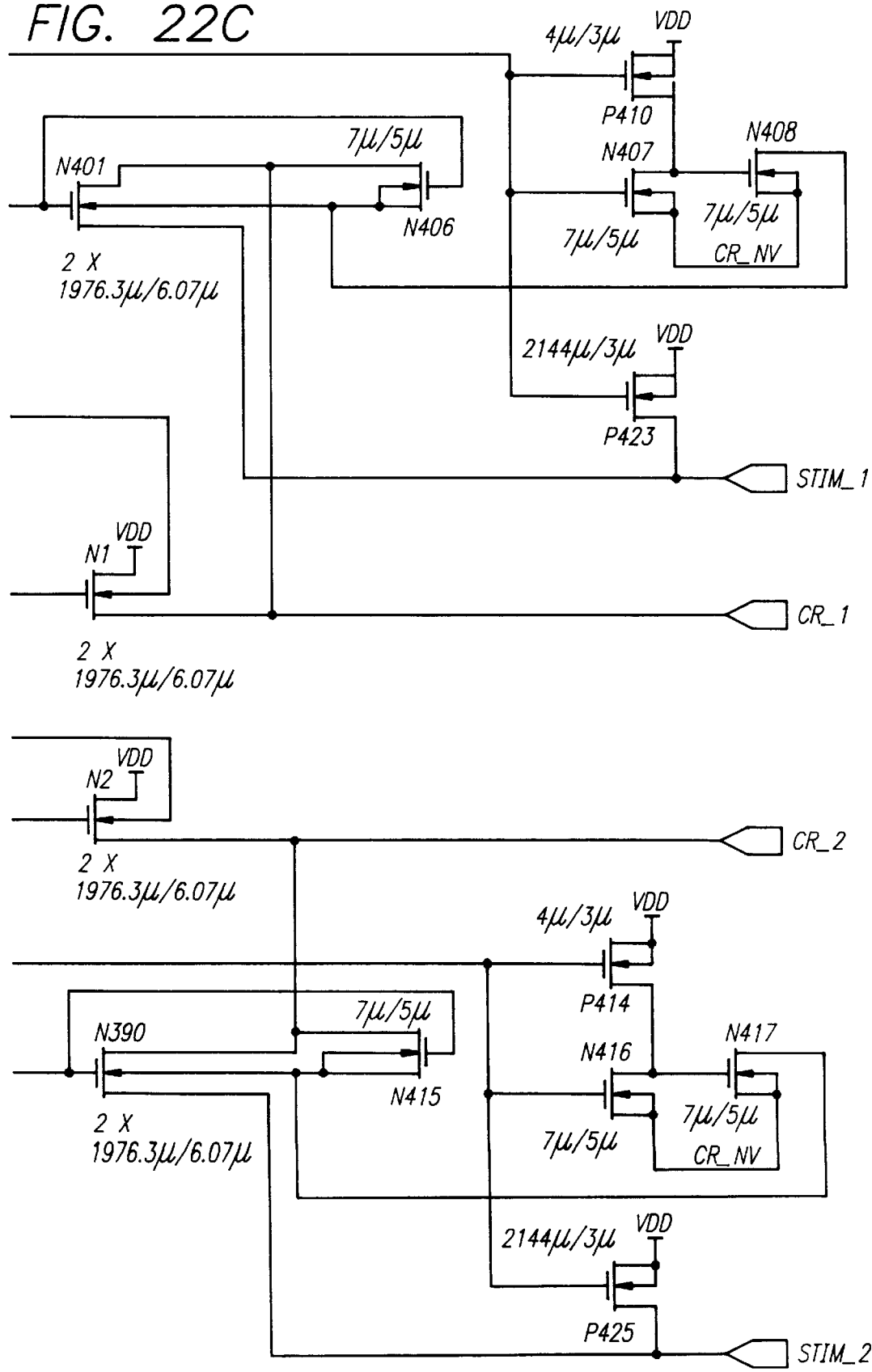

The idealistic representation of the DCI version of the implantable pulse generator 14 is depicted in FIG. 9. In this version of the implantable pulse generator 14, the pulse widths are digitally controlled by a timer. The implantable pulse generator 14 must be able to generate different amplitudes while preventing unwanted cross-conduction from occurring between different electrode switches during stimulation. In this version of the implantable pulse generator 14, only one of the channels of electrode switches are stimulated at any given time by the implantable pulse generator 14.

The programmed amplitude of the signal output of each channel of the DCI implantable pulse generator 14 is stored across two different capacitors, C2 and C3. These capacitors C2 and C3 are commonly referenced to the same node AMP_OUT. Therefore, AMP1 and AMP2 represent the two amplitudes (voltages) that are stored across capacitors C2 and C3. The 183 ohm resistor and switch 52 is used to discharge all or a portion of the charge on capacitors C2 and C3, thereby reducing the 15 stored amplitude(s). Similarly, the switching regulator 50 is used to increase the charge, and thus amplitude, on capacitors C2 and C3.

Thus, in order to use the electrodes (TPE) on channel 1 ("CH1") or channel 2 ("CH2") to stimulate the biological load or tissue "RL", switches N1 or N2 must first be respectively opened or closed. After switch N1 or N2 is closed, the tissue "RL" is stimulated when the stimulating switches (designated "S") or the stimulating/recharging switches (designated "S or R") are closed. After the stimulation pulse is complete, the system then waits a finite period of time before producing a recharging pulse. In the preferred embodiment, the finite period of time is 244 μsec.; however, a delay of 100 to 500 μsec. could be used. After the finite period of time elapses, the recharging switches (designated "R") or the "S or R" switches are closed in order to reverse the current through the tissue "RL", or in other words to recharge the tissue. The reason for the finite period of time delay is to prevent the physiological cancellation of the stimulation effect. The detailed circuit configuration of the "S", "R", and "S or R" monolithic switches can be seen in FIG. 11.

Other than capacitors C2 and C3, the capacitors 54 depicted in FIG. 9 are used to maintain charge balance. Similarly, capacitors can be installed between the following terminal pairs in order to maintain charge balance: CPB1_1–CPB1_2 and CPB2_1–CPB2_2.

As previously mentioned, FIGS. 15–22 illustrate an alternative output circuit configuration for the implantable pulse generator 14 called "transverse tripolar stimulation." This circuit configuration allows both channels to be utilized in order to simultaneously provide different amplitudes, frequencies, repetition rates, and pulse widths to three electrodes (one reference electrode and two electrodes at different amplitudes).

In the preferred embodiment of the present invention, the system employs a programmer 20 which is coupled via a conductor 22 to a radio frequency antenna 24. This system permits attending medical personnel to select the various signal output options—such as amplitude, pulse width, frequency, and repetition rate—after implant using radio frequency communications. While the preferred system employs fully implanted elements, systems employing partially implanted generators and radio-frequency coupling may also be used in the practice of the present invention (e.g., similar to products sold by Medtronic, Inc. under the trademarks X-trel and Mattrix).

FIG. 2 is a cross-sectional view of spine 12 showing implantation of the distal end of insulated leads 16 and 18 which terminate in electrodes 16A and 18A within epidural space 26. The electrodes may be conventional percutaneous electrodes, such as PISCES® model 3487A sold by Medtronic, Inc. Also shown is the subdural space 28 filled with cerebrospinal fluid (cfs), bony vertebral body 30, vertebral arch 31, and dura mater 32. The spine also includes gray matter 34 and dorsal horns 36 and 37 and white matter, for example, dorsal columns 46 and dorsal lateral columns 47.

Referring to FIG. 8, signal P1 is applied to electrode 18A (FIG. 2) and signal P2 is applied to electrode 16A (FIG. 2). Although signals P1 and P2 are shown as pulses, they also may comprises sinusoidal signals. Pulses P1 and P2 are generated at different frequencies. When the electric fields resulting from P1 and P2 pass through the same point in space at different frequencies, there is a difference frequency electric field set up corresponding to the difference between the frequencies of the two signals. For example, if P1 is generated at 150 Hz and P2 is generated at 50 Hz, the resulting difference frequency will be 100 Hz which is in the physiologic range.

Amplitude A1 of P1 is adjustable independently from amplitude A2 of P2. For the case in which amplitudes A1 and A2 are equal, the amplitude of the resulting difference frequency electric field is twice the amplitude of the individual electric fields.

Figure 3:
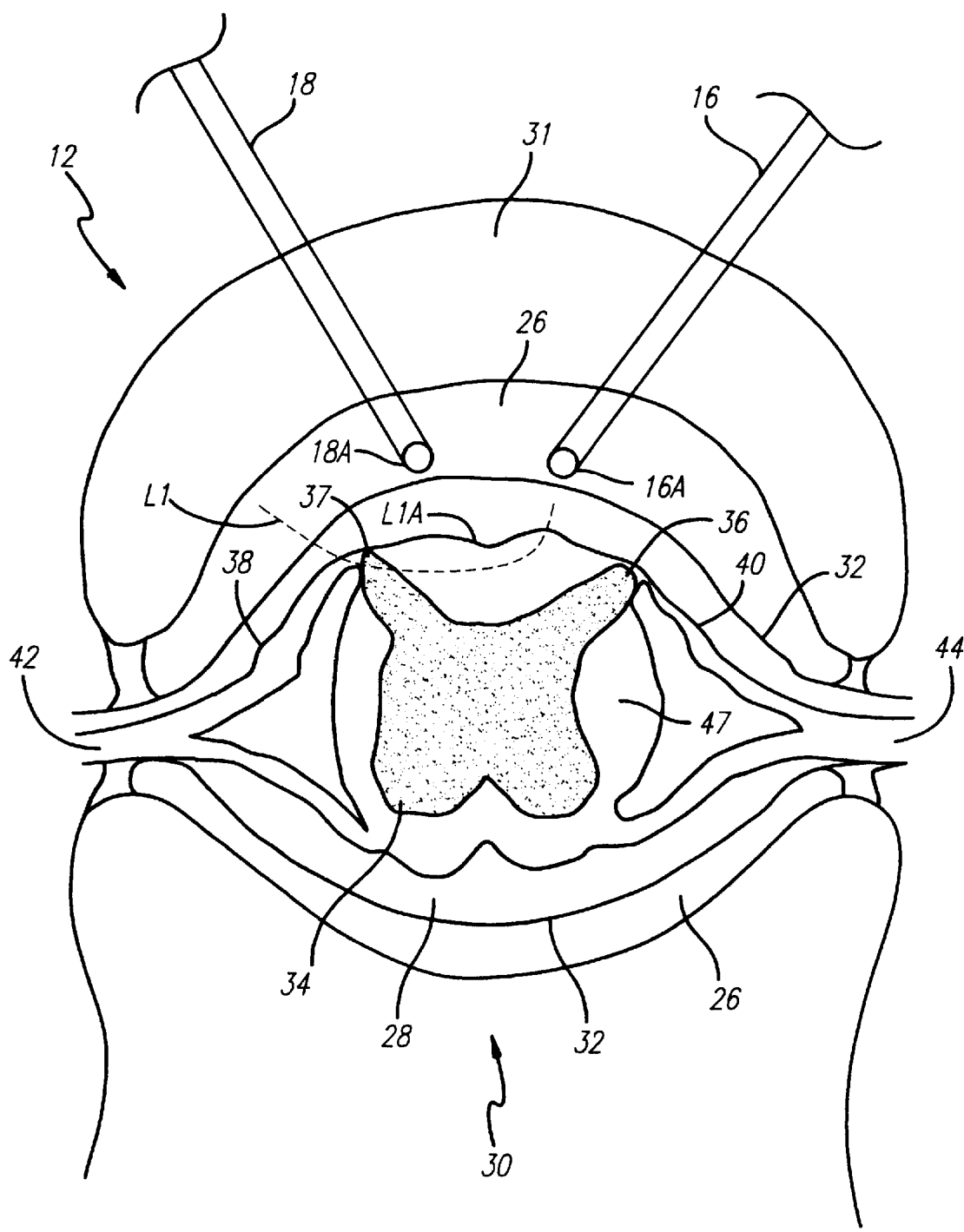
FIG. 3 is a cross-sectional view like FIG. 2 showing locus of potential changes induced in the spinal cord from a signal applied to a first one of two electrodes.

Referring to FIG. 3, line L1 represents the edge of a three-dimensional locus L1A in which pulse P1 applied to electrode 18A induces a potential PT1 between times T1 and T3 that is less than the transmembrane potential threshold TPT for cells of interest in that locus.

Figure 4:
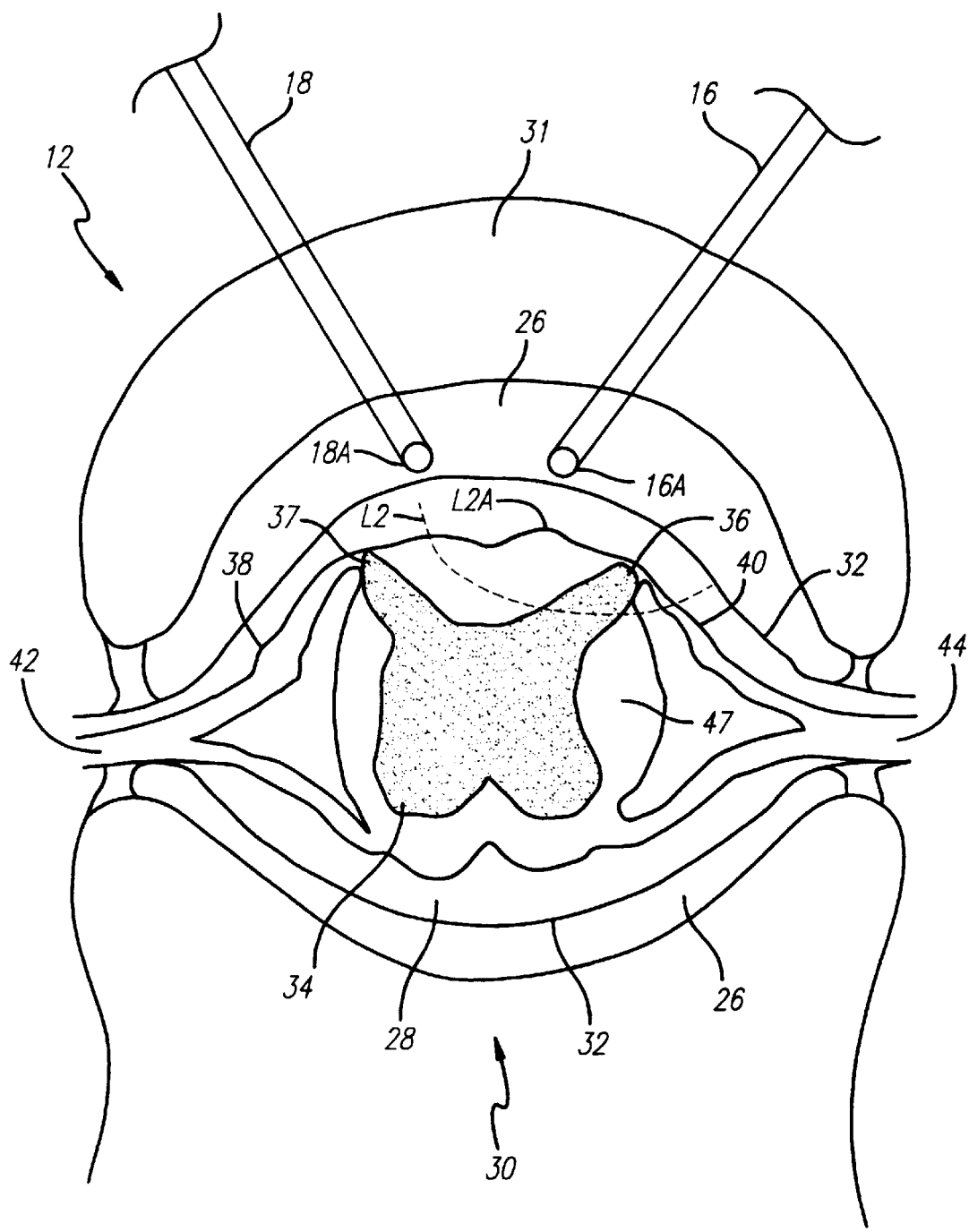
FIG. 4 is a view like FIG. 3 showing the locus of potential changes induced in the spinal cord from the application of a signal to the second of the electrodes.

Referring to FIG. 4, line L2 represents the edge of another three-dimensional locus L2A in which the application of pulse P2 (FIG. 8) to electrode 16A induces a depolarizing potential less than the transmembrane potential threshold TPT for cells of interest in that locus.

Figure 5:
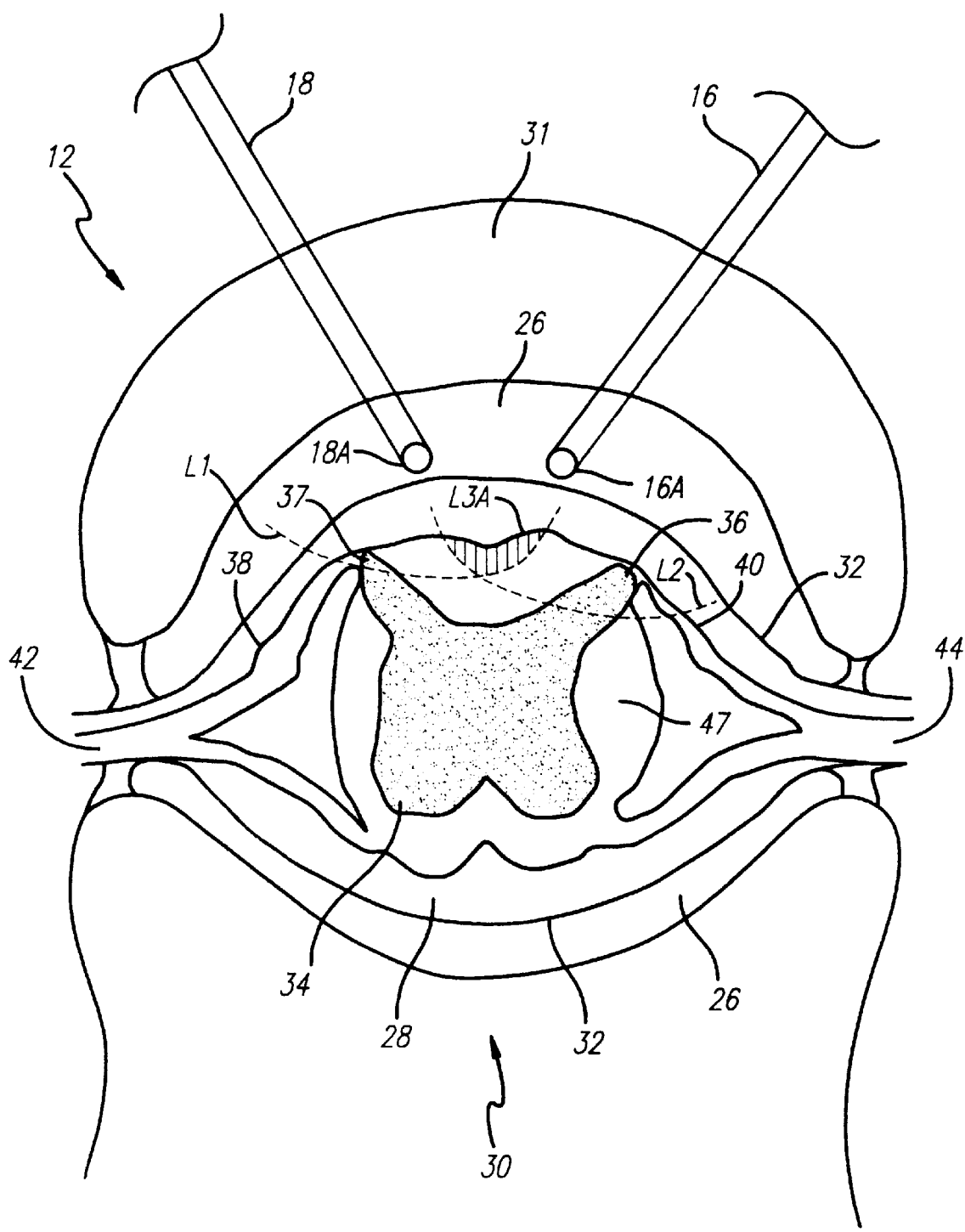
FIG. 5 is a view like FIG. 4 showing the combined loci in the spinal cord at which potentials are induced from signals applied to the first and second electrodes.

FIG. 5 illustrates a locus L3A representing the intersection of loci L1A and L2A in which the combined potentials induced in locus L3A from the difference frequency electric field produced by pulses P1 and P2 creates an action potential in cells of interest in locus L3A as illustrated by potential PT3 in FIG. 8. The potential induced in locus L1A outside locus L3A is illustrated by potential PT1 (FIG. 8). Since PT1 is lower than the transmembrane potential threshold TPT, there is no action potential created in locus L1A outside L3A. The potential created in locus in L2A outside L3A is illustrated by potential PT2 (FIG. 8). Since potential PT2 is less than the transmembrane potential threshold TPT, there is no action potential created in locus L2A outside locus L3A.

Figure 6:
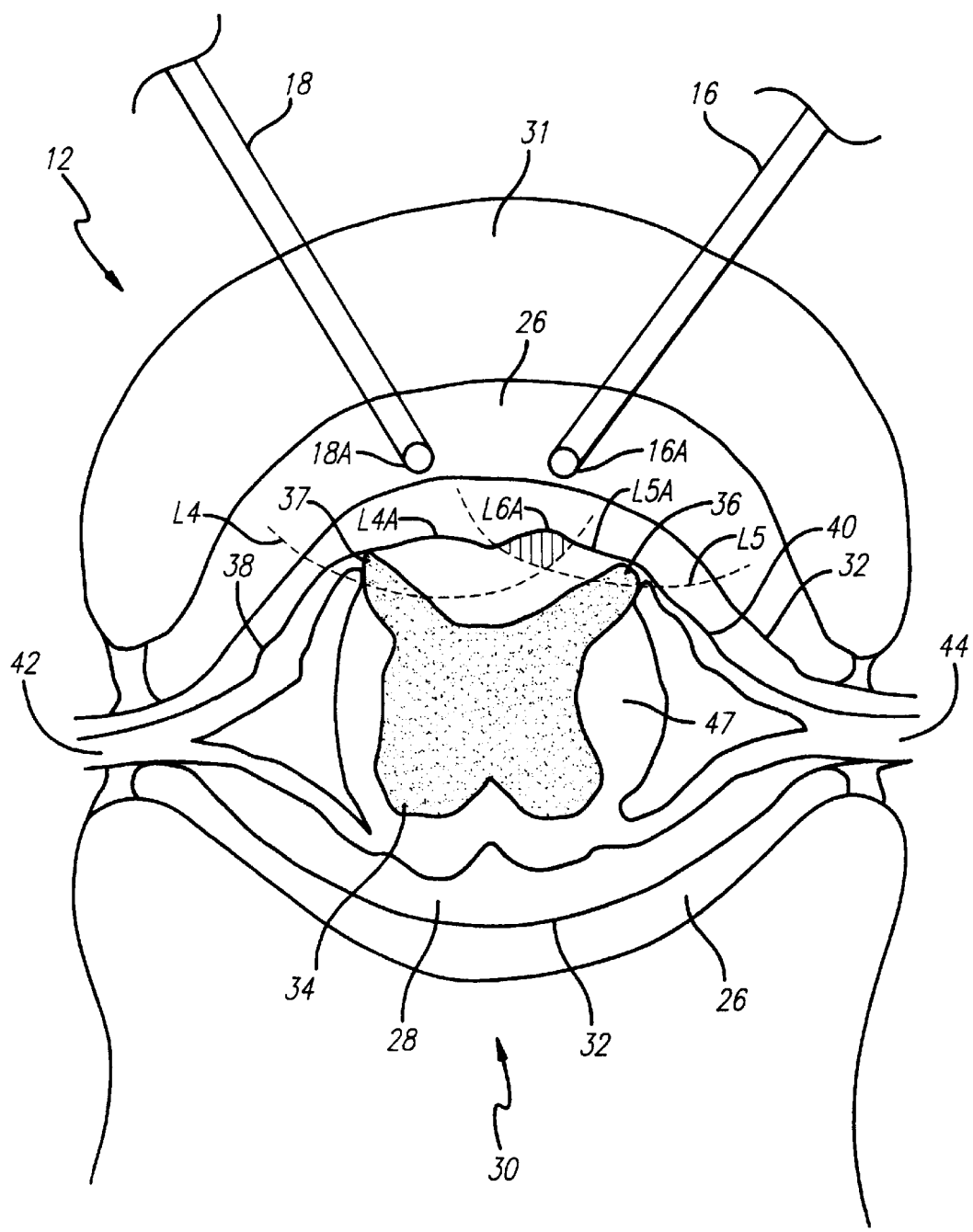
FIG. 6 is a view like FIG. 5 showing the alteration of the loci due to increase in the amplitude of the signal applied to the first electrode and a decrease in amplitude of the signal applied to the second electrode.

Referring to FIG. 6, line L4 represents the edge of another three-dimensional locus L4A resulting from the application of a pulse P1 to electrode 18A having an amplitude greater than amplitude A1 (FIG. 8), and line L5 represents the edge of another three-dimensional locus L5A resulting from the application of a pulse P2 to electrode 16A having an amplitude less than amplitude A2. The intersection of loci L4A and L5A represents a locus L6A resulting from the difference frequency electric field produced by pulses P1 and P2 in which action potentials are induced. Locus L6A is moved mostly to the right relative to locus L3A shown in FIG. 5. Action potentials are not induced outside locus L6A.

Figure 7:
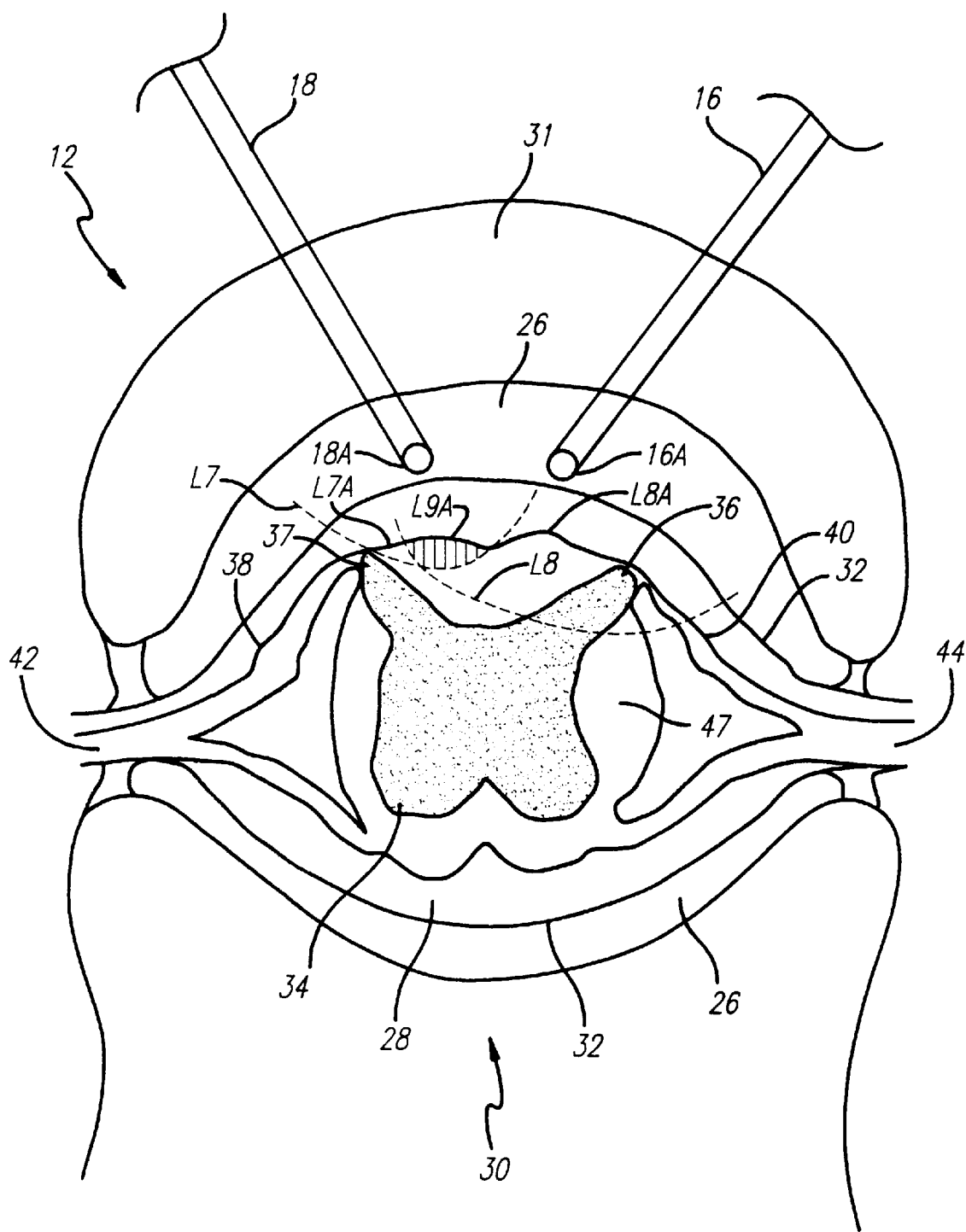
FIG. 7 is a view like FIG. 6 showing the alteration of the loci due to an increase in amplitude of the signal applied to the second electrode and a decrease in amplitude of the signal applied to the first electrode.

Referring to FIG. 7, line L8 represents the edge of another three-dimensional locus L8A resulting from the application of a pulse P2 to electrode 16A having an amplitude greater than amplitude A2 (FIG. 8), and line L7 represents the edge of another three-dimensional locus L7A resulting from the application of a pulse P1 to electrode 18A having an amplitude less than amplitude A1. The intersection of loci L7A and L8A represents a locus L9A resulting from the difference frequency electric field produced by pulses P1 and P2 in which action potentials are induced. It will be noted that the locus L9A is moved to the left compared with locus L3A shown in FIG. 5. Action potentials are not induced outside locus L9A.

The ability to move the locus in which action potentials are induced is an important feature. In many therapies, it is important to prevent action potentials being induced in gray matter 34 or dorsal horns 36 and 37, dorsal roots 38 and 40, dorsal lateral columns 47 or peripheral nerves 42 and 44 in order to minimize the possibility of causing pain, motor effects, or uncomfortable paresthesia. In the described techniques, the locus in which action potentials are induced (e.g., L3A, L6A or L9A) can be manipulated to a desired area of the dorsal columns 46 without inducing action potentials in dorsal horns 36 and 37, gray matter 34 or dorsal lateral columns 47. Moreover, the ability to move the locus in which action potentials are induced drastically reduces the accuracy necessary for surgically implanting electrodes 16A and 18A, and may eliminate the need for surgical lead revisions.

The foregoing techniques also may be applied to all electrically excitable tissue. Those skilled in the art will recognize that the preferred embodiments may be altered and amended without departing from the true spirit and scope of the appended claims.

We claim:

1. A method for therapeutically treating a patient by alternately stimulating and recharging a first pair of electrodes and a second pair of electrodes, the first and second pairs of electrodes optionally sharing a common electrode, the first pair of electrodes being operatively coupled and responsive to a first circuit including a first plurality of switches, the second pair of electrodes being operatively coupled and responsive to a second circuit including a second plurality of switches, the method comprising:

a. stimulating the first pair of electrodes;
   b. recharging the first circuit through the first pair of electrodes after stimulating the first pair of electrodes;
   c. waiting a finite period of time after recharging the first circuit through the first pair of electrodes;
   d. stimulating the second pair of electrodes;
   e. recharging the second circuit through the second pair of electrodes after stimulating the second pair of electrodes;
   f. waiting a finite period of time after recharging the second circuit through the second pair of electrodes;
   g. repeating steps a through f;
   h. opening each switch of the first plurality of switches during steps c, d, e, and f;
   I. opening each switch of the second plurality of switches during steps a, b, c, and f,
   j. closing a first subset of switches of the first plurality of switches during step a; and
   k. closing a second subset of switches of the second plurality of switches during step e.

2. The method of therapeutically treating a patient as in claim 1, further comprising the steps of:

l. closing a first subset of switches of the second plurality of switches during step d; and
   m. closing a second subset of switches of the second plurality of switches during step e.

3. The method of therapeutically treating a patient as in claim 2, further comprising the step of:

n. closing at least one switch of the first subset of switches of the first plurality of switches during both steps j and k.

4. The method of therapeutically treating a patient as in claim 3, further comprising the step of:

n. closing at least one switch of the first subset of switches of the second plurality of switches during both steps l and m.

5. A system for therapeutically treating a patient, comprising:

a first electrical circuit for stimulating and recharging using a first pair of electrodes;
   a second electrical circuit for stimulating and recharging using a second pair of electrodes, the first and second pairs of electrodes optionally sharing a common electrode;
   the first circuit including a first plurality of switches adapted to be opened during stimulation and recharging using the second pair of electrodes such that a relatively high impedance is created across the first pair of electrodes thereby substantially preventing current from flowing through the first pair of electrodes during stimulation and recharging using the second pair of electrodes, a subset of the first plurality of switches being adapted to be closed during stimulating and recharging using the first pair of electrodes; and
   the second circuit including a second plurality of switches adapted to be opened during stimulation and recharging using the first pair of electrodes such that a relatively high impedance is created across the second pair of electrodes thereby substantially preventing current from flowing through the second pair of electrodes during stimulation and recharging using the first pair of electrodes, a subset of the second plurality of switches being adapted to be closed during stimulating and recharging using the second pair of electrodes.

6. Apparatus for therapeutically treating a patient, comprising:

means for stimulating and recharging using a first pair of electrodes, the means for stimulating and recharging using the first pair of electrodes including a first plurality of switches adapted to be closed during both stimulating and recharging using the first pair of electrodes;
   means for stimulating and recharging using a second pair of electrodes, the means for stimulating and recharging using the second pair of electrodes including a second plurality of switches adapted to be closed during both stimulating and recharging using the second pair of electrodes;
   means for creating a high impedance state across the first pair of electrodes while the means for stimulating and recharging using the second pair of electrodes are stimulating or recharging; and
   means for creating a high impedance state across the second pair of electrodes while the means for stimulating and recharging using the first pair of electrodes are stimulating or recharging.

7. The apparatus as in claim 6, further comprising:

means for introducing a delay between activating the means for stimulating and recharging the first pair of electrodes and activating the means for stimulating and recharging the second pair of electrodes.

* * * * *